United States Patent
Margolis et al.

(10) Patent No.: US 11,977,084 B2
(45) Date of Patent: May 7, 2024

(54) NERVOUS SYSTEM-SPECIFIC TRANSMEMBRANE PROTEASOME COMPLEX THAT MODULATES NEURONAL SIGNALING THROUGH EXTRACELLULAR SIGNALING VIA BRAIN ACTIVITY PEPTIDES

(71) Applicant: THE JOHNS HOPKINS UNIVERSITY, Baltimore, MD (US)

(72) Inventors: Seth S. Margolis, Towson, MD (US); Kapil V. Ramachandran, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 427 days.

(21) Appl. No.: 17/005,892

(22) Filed: Aug. 28, 2020

(65) Prior Publication Data
US 2020/0393471 A1 Dec. 17, 2020

Related U.S. Application Data

(62) Division of application No. 15/550,632, filed as application No. PCT/US2016/017525 on Feb. 11, 2016, now Pat. No. 10,775,391.

(60) Provisional application No. 62/114,758, filed on Feb. 11, 2015.

(51) Int. Cl.
| | | |
|---|---|---|
| *G01N 33/68* | (2006.01) | |
| *A61K 31/165* | (2006.01) | |
| *A61K 31/69* | (2006.01) | |
| *A61K 38/05* | (2006.01) | |
| *A61K 51/00* | (2006.01) | |
| *G01N 30/72* | (2006.01) | |
| *G01N 30/88* | (2006.01) | |
| *G01N 33/50* | (2006.01) | |

(52) U.S. Cl.
CPC ....... *G01N 33/6896* (2013.01); *A61K 31/165* (2013.01); *A61K 31/69* (2013.01); *A61K 38/05* (2013.01); *A61K 51/00* (2013.01); *G01N 30/72* (2013.01); *G01N 33/5023* (2013.01); *G01N 33/5058* (2013.01); *G01N 2030/8831* (2013.01); *G01N 2333/47* (2013.01); *G01N 2800/2821* (2013.01)

(58) Field of Classification Search
CPC ....... G01N 33/6896; G01N 2800/2821; G01N 33/5023; G01N 33/5058; G01N 2333/47; A61K 31/165; A61K 31/69; A61K 38/05; A61K 51/00
See application file for complete search history.

(56) References Cited

U.S. PATENT DOCUMENTS 7,902,185 B2   3/2011  Ramesh et al.

OTHER PUBLICATIONS

Besche, H., et al., "Isolation of Mammalian 26S Proteasomes and p97/VCP Complexes Using the Ubiquitin-like Domain from HHR23B Reveals Novel Proteasome-Associated Proteins" Biochemistry 2009, 48, 2538-2549.
Blasdel, G., et al., "Voltage-sensitive dyes reveal a modular organization in monkey striate cortex" Nature vol. 321, 1986.
Cai, F., et al., "Protein degradation by the proteasome is required for synaptic tagging and the heterosynaptic stabilization of hippocampal late-phase long-term potentiation" Neuroscience 169 (2010) 1520-1526.
Ciechanover, A., "The ubiquitin-proteasome pathway: on protein death and cell life" The EMBO Journal vol. 17 No.24 pp. 7151-7160, 1998.
Ciechanover, A., et al., "The ubiquitin-proteasome pathway: The complexity and myriad functions of proteins death" Proc. Natl. Acad. Sci. USA vol. 95, pp. 2727-2730, Mar. 1998.
Coux, O., "Structure and functions of the 20s and 26s proteasomes" Annu. Rev. Biochem, 1996, 65:801-847.
Dong, C., et al., "Proteasome inhibition enhances the induction and impairs the maintenance of late-phase long-term potentiation" Learnmem, 2008, 15:335-347.
Ehlers, M., "Activity level controls postsynaptic composition and signaling via the ubiquitin-proteasome system" nature neuroscience • vol. 6 No 3 • Mar. 2003.
Huang, L., et al., "Proteasome regulators: activators and inhibitors" Curr Med Chem. 2009 ; 16(8): 931-939.
Margolis, S., et al., "EphB-Mediated Degradation of the RhoA GEF Ephexin5 Relieves a Developmental Brake on Excitatory Synapse Formation", Cell 143, 442-455, Oct. 29, 2010.

(Continued)

*Primary Examiner* — Olga N Chernyshev
(74) *Attorney, Agent, or Firm* — Johns Hopkins Technology Ventures

(57) ABSTRACT

The inventors surprisingly found that neural stimulation caused the synthesis and degradation of proteins into peptides which were then secreted into the cell media within minutes of stimulation by a novel neural-specific and membrane bound proteasome (neuronal membrane proteasome or NMP) that is transmembrane in nature. These secreted, activity-induced, proteasomal peptides (SNAPPs) range in size from about 500 Daltons to about 3000 Daltons. Surprisingly none of the peptides appear to be those previously known to have any neuronal function. Moreover, these SNAPPs have stimulatory activity and are heretofore a new class of signaling molecules. Moreover, the NMP appears to play a highly significant role in aspects of neuronal signaling known to be critical for neuronal function. The inventors have gone on to develop all tools to study this novel mechanisms including protocols and practice for generation and purification of SNAPPs as well as a new and specific inhibitor of the NMP allowing for selective control of this process in the nervous system. The present invention provides methods of making and using these SNAPPs for both laboratory and clinical purposes, the screening for molecules which modulate NMP function in vivo and in vitro, and methods for diagnosis of NMP related diseases.

3 Claims, 15 Drawing Sheets

(56) References Cited

OTHER PUBLICATIONS

Rinetti, G., et al., "Ubiquitination Acutely Regulates Presynaptic Neurotransmitter Release in Mammalian Neurons" The Journal of Neuroscience, Mar. 3, 2010 • 30(9):3157-3166.

Scheper, G., et al., "Translation matters: protein synthesis defects in inherited disease" Nature Reviews/Genetics, vol. 8, 2007.

Wang, H., et al., "Regulation of Cell Polarity and Protrusion Formation by Targeting RhoA for Degradation" Science, vol. 302, 2003.

Willeumier, K., et al., "Proteasome Inhibition Triggers Activity-Dependent Increase in the Size of the Recycling Vesicle Pool in Cultured Hippocampal Neurons" The Journal of Neuroscience, Nov. 1, 2006 • 26(44):11333-11341.

Otero et al., 'Fast axonal transport of the proteasome complex depends on membrane interaction and molecular motor function' Journal of Cell Science, vol. 127, pp. 1537-1549 (2014).

Tai et al., 'Ubiquitin, the proteasome and protein degradation in neuronal function and dysfunction' Nature Reviews Neuroscience, vol. 9, pp. 826-838 (2008).

Hegde et al., 'Role of ubiquitin-proteasome-mediated proteolysis in nervous system disease' Biochimica et Biophysica Acta, vol. 1809, pp. 128-140 (2011).

Lin et al., 'Ubiquitination of neurotransmitter receptors and post-synaptic scaffolding proteins' Neural Plasticity, vol. 2013, Article ID.432057, pp. 1-10 (2013).

Ben-Nissan et al., 'Regulating the 20S proteasome ubiquitin-independent degradation pathway' Biomolecules, vol. 4, pp. 862-884 (2014).

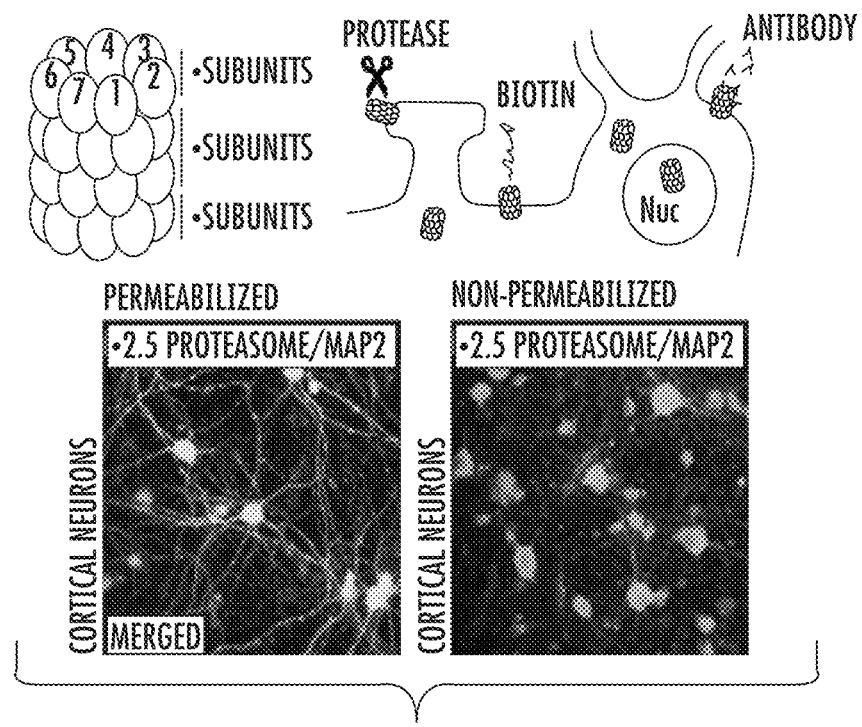
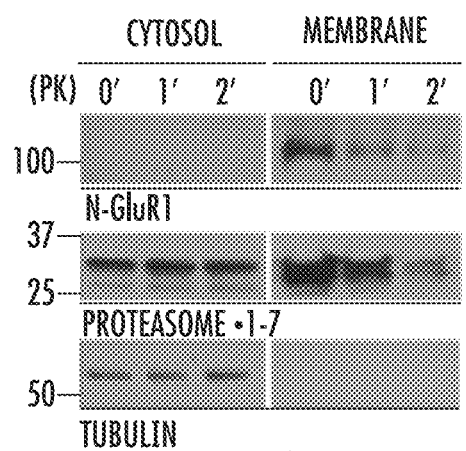
FIG. 2A
FIG. 2B
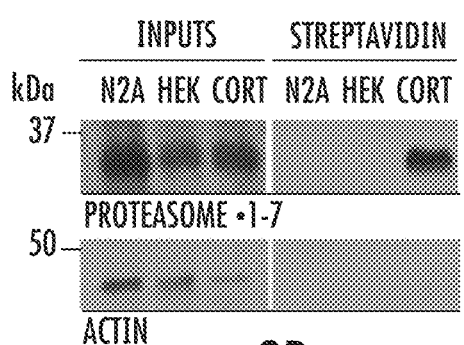
FIG. 2D
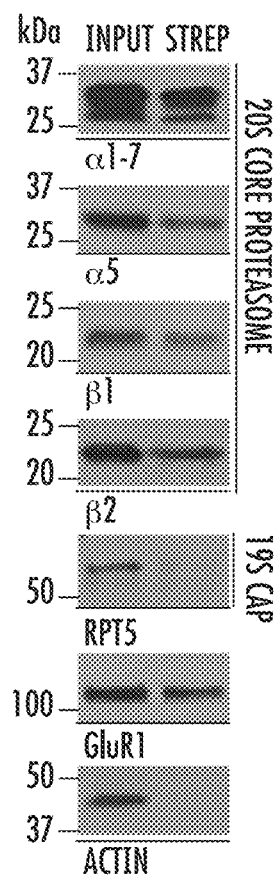
FIG. 2C

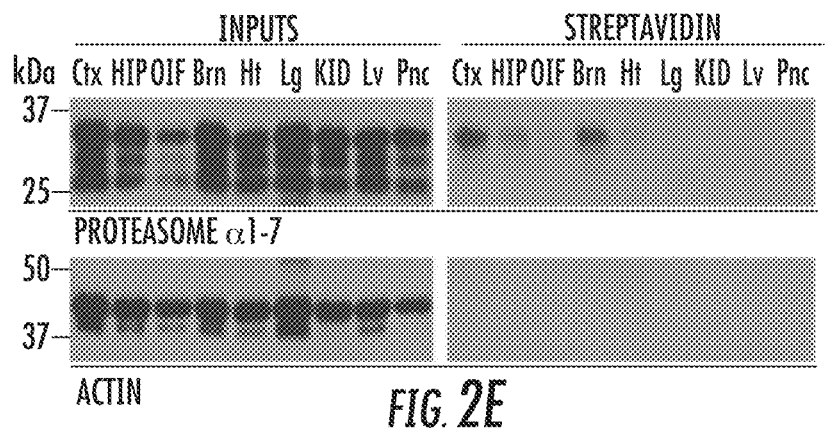

FIG. 2E

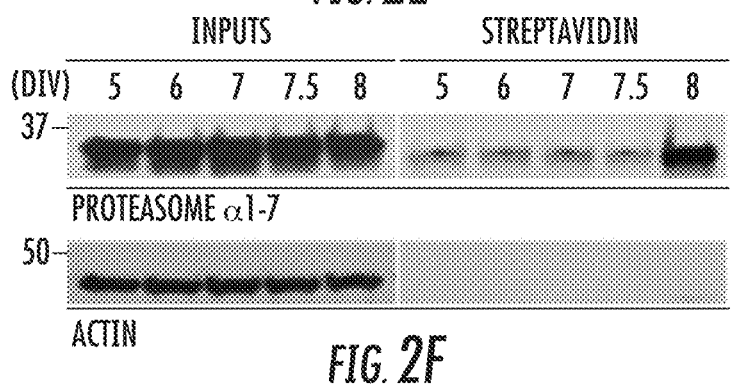

FIG. 2F

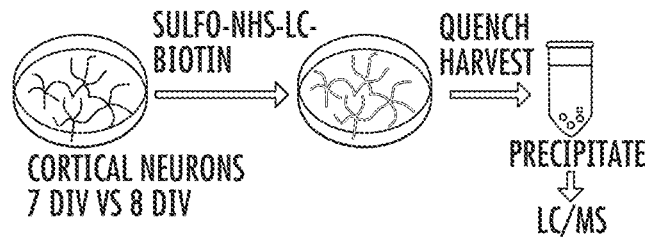

| PROTEIN ID | PROTEIN NAME | MW | % COVERAGE |
|---|---|---|---|
| PSA1 | PROTEASOME SUBUNIT α1 | 29528 | 39.9 |
| PSA3 | PROTEASOME SUBUNIT α3 | 28387 | 18.4 |
| PSA4 | PROTEASOME SUBUNIT α4 | 29452 | 30.3 |
| PSA5 | PROTEASOME SUBUNIT α5 | 26394 | 25.3 |
| PSA6 | PROTEASOME SUBUNIT α6 | 27355 | 28.9 |
| PSA7 | PROTEASOME SUBUNIT α7 | 27838 | 21.8 |
| PSB1 | PROTEASOME SUBUNIT β1 | 26355 | 28.3 |
| PSB2 | PROTEASOME SUBUNIT β2 | 22892 | 10.4 |
| PSB3 | PROTEASOME SUBUNIT β3 | 22949 | 19.5 |
| PSB4 | PROTEASOME SUBUNIT β4 | 29097 | 17.8 |
| PSB5 | PROTEASOME SUBUNIT β5 | 28514 | 27.7 |
| PSB6 | PROTEASOME SUBUNIT β6 | 25362 | 33.2 |
| PSB7 | PROTEASOME SUBUNIT β7 | 29872 | 24.2 |

FIG. 2G

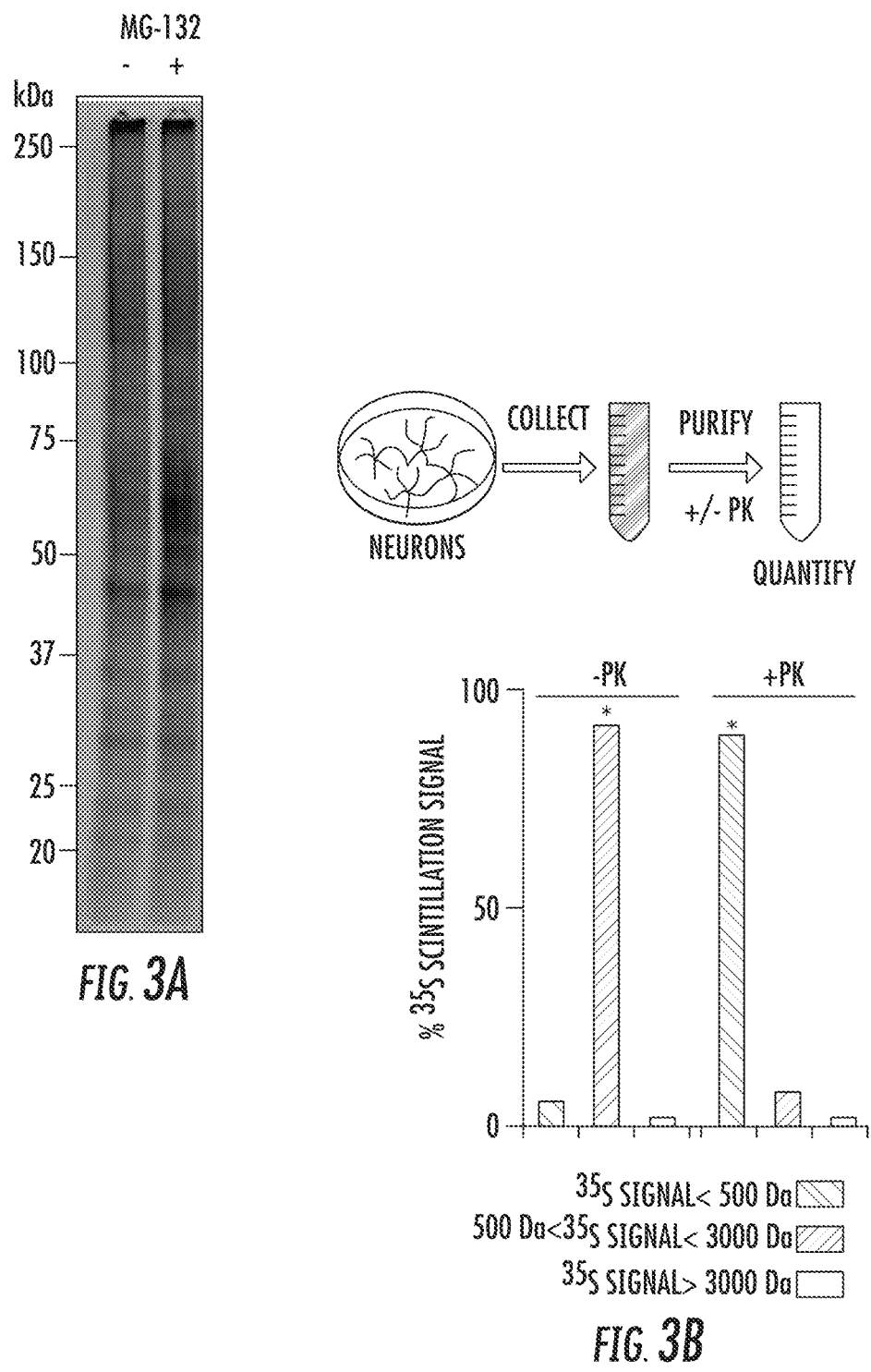

NERVOUS SYSTEM-SPECIFIC TRANSMEMBRANE PROTEASOME COMPLEX THAT MODULATES NEURONAL SIGNALING THROUGH EXTRACELLULAR SIGNALING VIA BRAIN ACTIVITY PEPTIDES

REFERENCE TO RELATED APPLICATIONS

This application is a Divisional of U.S. patent application Ser. No. 15/550,632, filed Aug. 11, 2017, which is a 35 U.S.C. § 371 U.S. national entry of International Application PCT/US2016/017525, having an international filing date of Feb. 11, 2016, which claims the benefit of U.S. Provisional Application No. 62/114,758, filed Feb. 11, 2015, the content of each of the aforementioned applications is herein incorporated by reference in their entirety.

STATEMENT OF GOVERNMENTAL INTEREST

This invention was made with government support under grant no. 1R01MH102364, awarded by the National Institutes of Health. The government has certain rights in the invention.

BACKGROUND OF THE INVENTION

The ability to convert transient stimuli from the extracellular environment into long-term changes in neuronal function is central to an animal's capacity to adapt and learn from its environment. This is mediated through sensory organs which transduce physical and chemical stimuli into precise patterns of neuronal activity that elicit specific changes in the structure and function of the nervous system. Insight into the mechanisms that underlie these activity-dependent changes has been facilitated by the discoveries of many laboratories over the last several decades demonstrating that neurotransmitters released at neuronal synapses drive proteasome dependent protein degradation (J Biol Chem 284, 26655 (2009); Nat Neurosci 6, 231 (2003)). Consistent with a role for neural activity in regulating protein degradation, the proteasome localize to sites of synaptic activity (Nature 441, 1144 (2006)). This regulation is central to the ability of a neuron to appropriately respond to stimuli, as inhibition of protein degradation impairs a host of neuronal functions, ranging from plasticity at the Aplysia sensorimotor synapse to cell migration, neurotransmission, and physiology in the mammalian nervous system (Neuron 32, 1013-1026, 2001; Neuron 52, 239-245, 2006; Cell 89, 115-126, 1997; J Neurosci 26, 11333-11341, 2006) including the maintenance of long-term potentiation, a critical cellular mechanism underlying learning and memory (Neuron 52, 239 (2006); Nat Neurosci 9, 478 (2006)). Moreover, mutations in components of protein degradation machinery cause profound defects in human cognitive function (Biochim Biophys Acta 1843, 13 (2014); Nat Rev Genet 8, 711 (2007)).

However, roles for proteasome function in the nervous system are more complex than they may appear. Proteasome function is required for certain aspects of nervous system function over long timescales (hours to days), such as synaptic remodeling and cell migration (Nat Neurosci 6, 231-242, 2003; Science 302, 1775-1779, 2003). Contrastingly, proteasome function is also required for activity-dependent neuronal processes over very short timescales (seconds to minutes), such as regulating the speed and intensity of neuronal transmission or the maintenance of long-term potentiation (Nature 441, 1144-1148, 2006; Neuroscience 169, 1520-1526, 2010; J Biol Chem 284, 26655-26665, 2009; Learn Mem 15, 335-347, 2008; J Neurosci 26, 4949-4955, 2006; J Neurosci 30, 3157-3166, 2010).

Proteasomes are heterogeneous multisubunit catalytic complexes that consist of a core 20S stacked ring of α/β subunits with a $\alpha_7\beta_7\beta_7\alpha_7$ architecture, and can be associated with 19S or 11S regulatory cap-particles to form a 26S proteasome (Ann. Rev Biochem 65, 801-847, 1996). While the natural behavior of 26S capped proteasomes is to mediate ATP-dependent degradation of ubiquitinated proteins, 20S uncapped proteasomes do not require ubiquitin or ATP for their catalytic function (Biomolecules 4, 862-884, 2014; EMBO J 17, 7151-7160, 1998; Proc Natl Acad Sci USA 95, Proc Natl Acad Sci USA 95, 2727-2730 2727-2730, 1998) Recent studies have shown that 20S proteasomes may have key biological functions separate from the canonical 26S ubiquitin-proteasome degradation pathway, particularly in clearing unstructured proteins and in degrading proteins during cellular stress (Ben-Nissan and Sharon, 2014). Despite extensive studies on proteasome function in neuronal signaling, the role of the 20S proteasome in the nervous system has remained unknown.

Critically, the functional studies addressing the role for proteasomes in the nervous system have either failed to discriminate between 20S and 26S proteasomes through the use of pan-proteasome inhibitors such as MG-132 or lactacystin, or have focused on the 26S proteasome through altering the ubiquitination pathway. Despite these and other efforts to understand the role of proteasomes in the nervous system, distinct proteasomes that potentially function independent of their proteostatic role to mediate rapid neuronal signaling have not been discovered. Therefore, we considered that taking an unbiased approach to evaluating proteasomes in the nervous system, without bias for 20S or 26S proteasomes, would provide a means to identify unique proteasomes that could possibly have acute signaling functions.

There exists an unmet need for better understanding protein degradation in neurons and its link to cognitive function and neuronal signaling in health and disease.

SUMMARY OF THE INVENTION

The present inventors made the surprising observation that acute addition of the proteasome inhibitor MG-132 onto neurons suppressed neuronal activity-induced calcium signaling within seconds. Since short-term inhibition of the proteasome presumably cannot meaningfully change the overall protein landscape, it was unclear how proteasomes can rapidly alter neuronal function. Thus, the inventors reasoned that an unidentified function for proteasomes in the nervous system must exist.

The present inventors' investigation revealed a novel neuronal-specific 20S proteasome complex that was expressed at neuronal plasma membranes and exposed to the extracellular space. It was found that the activity of this novel neural membrane bound proteasome (NMP) converted intracellular proteins into extracellular peptides that rapidly induced neuronal signaling. Specific inhibition of this NMP through a novel membrane-impermeable proteasome inhibitor rapidly attenuated activity-induced neuronal function. These findings identify a new signaling modality in the nervous system and unveil the possibility that the membrane proteasome may be responsible for the previously observed decades of research showing that acute proteasome-mediated effects on nervous system function.

The present inventors monitored the fate of synthesized proteins and found that degradation of proteins by the NMP produced peptides which were directly released into the cell media. Hypothesizing that the NMP may play a role in neuronal activity-dependent mechanisms of nervous system function the inventors found that this release was suppressed when neuronal activity was blocked. Consistent with this finding, the release of these peptides into the media was dramatically enhanced in response to neuronal stimulation. These secreted, neuronal activity-induced, proteasomal peptides (SNAPPs) range in size from about 500 Daltons to about 3000 Daltons. Surprisingly none of these peptides produced by the NMP appear to be those previously known. Moreover, these SNAPPs have stimulatory activity and are heretofore a new class of signaling molecules.

Taken together this discovery defines a new modality of critical neuronal communication through production of biologically meaningful peptides, SNAPPs, that requires the function of a novel neuronal specific transmembrane proteasome, NMP. Changes in the NMP level and possibly activity greatly impact SNAPP production and activity dependent neuronal signaling critical for nervous system function.

The present inventors used their developed protocols and reagents to determine whether the NMP was disrupted in various neurodegenerative disorders. They found decreased NMP levels in AD human brains and in vitro model systems for AD. They found decreased NMP in Huntington disease mouse models as well. These data are consistent with changes in the NMP level contributing to neurodegeneration and/or serving as a biomarker for detecting the development of these or other NMP associated disorders.

In accordance with an embodiment, the present invention provides a method for diagnosing a NMP associated disease or disorder of neuronal cells in a subject comprising: a) obtaining a sample of neuronal tissue from the subject; b) isolating the surface proteins of the neuronal tissue; c) analyzing the surface proteins of b) for the quantity of expression of one or more 20S protein core subunit proteins; d) providing a reference neuronal tissue sample; e) comparing the quantity of expression of one or more 20S protein core subunit proteins from the sample of a) to the quantity of expression of one or more 20S protein core subunit proteins from the reference sample; and f) identifying the subject as having a NMP associated disease or disorder of neuronal cells when the quantity of expression of one or more 20S protein core subunit proteins from the neuronal tissue sample of the subject is significantly greater or less than the quantity of expression of one or more 20S protein core subunit proteins from the reference sample.

In accordance with an embodiment, the present invention provides a method for diagnosing degenerative disease or disorder of neuronal cells in a subject comprising: a) obtaining a sample of neuronal tissue from the subject; b) isolating the surface proteins of the neuronal tissue; c) analyzing the surface proteins of b) for the quantity of expression of one or more 20S protein core subunit proteins; d) providing a reference neuronal tissue sample; e) comparing the quantity of expression of one or more 20S protein core subunit proteins from the sample of a) to the quantity of expression of one or more 20S protein core subunit proteins from the reference sample; and f) identifying the subject as having a degenerative disease or disorder of neuronal cells when the quantity of expression of one or more 20S protein core subunit proteins from the neuronal tissue sample of the subject is significantly less than the quantity of expression of one or more 20S protein core subunit proteins from the reference sample.

In accordance with another embodiment, the present invention provides a method for identifying a human subject as having a NMP associated disease or disorder of neuronal cells comprising: a) obtaining a biological sample from said human subject; b) quantifying the amount of SNAPPs in the sample from a); c) comparing the amount of SNAPPs in the sample from a) to the amount of SNAPPs in samples from normal control subjects; and d) identifying the subject as having a NMP associated disease or disorder of neuronal cells when the quantity of SNAPPs in the sample from a) is significantly greater or less than the quantity of SNAPPs in samples from normal control subjects.

In accordance with an embodiment, the present invention provides a composition comprising one or more secreted cortical neuronal-activity induced proteasomal peptides (SNAPPs).

In accordance with another embodiment, the present invention provides a composition comprising one or more secreted neuronal-activity induced proteasomal peptides (SNAPPs) and at least one detectable moiety.

In accordance with still another embodiment, the present invention provides a method for making secreted neuronal-activity induced proteasomal peptides (SNAPPs) comprising the steps of: a) providing an in vitro culture of a plurality of cortical neurons in a growth medium; b) stimulating the neurons for a period of time sufficient to allow secretion of SNAPPs into the growth medium; c) removing at least a portion of the growth medium containing the SNAPPs.

In accordance with a further embodiment, the present invention provides a method for screening for compounds which stimulate NMP and subsequent production of secreted cortical neuronal-activity induced proteasomal peptides (SNAPPs) comprising the steps of: a) providing a plurality of in vitro cultures comprising a plurality of neurons in a growth medium; b) providing one or more test cultures by contacting the neurons of at least a first culture with a test compound for a period of time sufficient to stimulate NMP and allow production of SNAPPs into the growth medium; c) providing a negative control by contacting the neurons of at least a second culture for a period of time sufficient with a carrier or vehicle which will not stimulate NMP mediated production of SNAPPs into the growth medium; d) removing at least a portion of the growth medium of the cultures of b) and c) and performing an isolation step to purify the SNAPPs from the cultures of b) and c); e) quantifying the amount of SNAPPs isolated in e) from the cultures of b) and c); and f) determining that the test compound is a stimulator of NMP mediated SNAPP production when the quantity of SNAPPs isolated from b) are significantly increased when compared with the amount of SNAPPs in c).

In accordance with a further embodiment, the present invention provides a method for screening for compounds which stimulate NMP and subsequent production of secreted cortical neuronal-activity induced proteasomal peptides (SNAPPs) comprising the steps of: a) administering to a subject a test compound for a period of time sufficient to stimulate NMP and allow production of SNAPPs in the neurons of the subject; b) providing a negative control by administering to at least a second subject for a period of time sufficient with a carrier or vehicle which will not stimulate NMP mediated production of SNAPPs in the neurons of the second subject; c) obtaining a biological sample from a) and b) and performing an isolation step to purify the SNAPPs from the biological samples of b) and c); d) quantifying the amount of SNAPPs isolated in e) from the biological samples of a) and b); and e) determining that the test compound is a stimulator of NMP mediated SNAPP production when the quantity of SNAPPs isolated from the biological samples of a) are significantly increased when compared with the amount of SNAPPs isolated from the biological samples of b).

In accordance with yet another embodiment, the present invention provides a method for screening for compounds which inhibit NMP mediated production of secreted neuronal-activity induced proteasomal peptides (SNAPPs) comprising the steps of: a) providing a plurality of in vitro cultures comprising a plurality of neurons in a growth medium; b) providing one or more test cultures by contacting the neurons of at least a first culture with a test compound and with a known neuronal stimulant of NMP for a period of time sufficient to allow NMP mediated production of SNAPPs into the growth medium; c) providing a negative control by contacting the neurons of at least a second culture for a period of time sufficient with a carrier or vehicle which will not stimulate NMP and secretion of SNAPPs into the growth medium; d) providing a positive control by stimulating the neurons of a third culture for a period of time sufficient with a known neuronal stimulant to allow NMP mediated production of SNAPPs into the growth medium; e) removing at least a portion of the growth medium of the cultures of b) to d) and performing an isolation step to purify the SNAPPs from the cultures of b) to d); f) quantifying the amount of SNAPPs isolated in e) from the cultures of b) to d); and g) determining that the test compound is an inhibitor of NMP mediated SNAPP production when the quantity of SNAPPs isolated from b) are significantly reduced when compared with the amount of SNAPPs in c) and/or d).

In accordance with another embodiment, the present invention provides a method for screening for compounds which inhibit NMP mediated production of secreted neuronal-activity induced proteasomal peptides (SNAPPs) in a subject comprising the steps of: a) administering to a first subject a test compound thought to be an inhibitor of NMP for a period of time sufficient to allow NMP mediated production of SNAPPs in the subject; b) providing a negative control by administering to at least a second subject for a period of time sufficient with a carrier or vehicle which will not stimulate NMP and secretion of SNAPPs in the second subject; c) providing a positive control by administering to at least a third subject for a period of time sufficient with a known neuronal stimulant to allow NMP mediated production of SNAPPs in the subject; d) obtaining biological samples from the subjects of a) to c) and performing an isolation step to purify the SNAPPs from the biological samples of a) to c); e) quantifying the amount of SNAPPs isolated in d) from the biological samples of a) to c); and f) determining that the test compound is an inhibitor of NMP mediated SNAPP production when the quantity of SNAPPs isolated from the biological samples of a) are significantly reduced when compared with the amount of SNAPPs isolated from the biological samples of b) and/or c).

In accordance with an embodiment, the present invention provides a method for inhibiting secreted neuronal-activity induced proteasomal peptides (SNAPPs) in a neuronal cell or population of cells comprising contacting the cell or population of cells with an effective amount of at least one NMP inhibitor for a time sufficient to inhibit secretion of SNAPPs.

In accordance with another embodiment, the present invention provides a method for identifying and targeting activated neurons in vitro comprising: a) providing a plurality of in vitro cultures comprising a plurality of neurons in a growth medium; b) stimulating at least one or more of the cultures with a stimulant; c) removing the growth medium of the plurality of in vitro cultures; d) fixing the plurality of in vitro cultures; e) staining the plurality of in vitro cultures with at least one or more SNAPP compositions as described herein; f) quantifying the detectable moiety of the compositions of e) using imaging and/or radiography; g) identifying the activated neurons as those neurons from stimulated in vitro cultures which have a significantly increased amount of detectable signal from the detectable moiety compared to the amount of detectable signal in neurons from in vitro cultures which were not stimulated; and h) using the ability of SNAPPs to bind to activated neurons to target a conjugated molecule to activated neurons.

In accordance with an embodiment, the present invention provides a method for identifying and targeting activated neurons in vivo using the ability of SNAPPs to bind to activated neurons to target a conjugated molecule to activated neurons, comprising: a) administering to the neuronal tissue of a mammal an effective amount of at least one or more SNAPP compositions as described herein, wherein the imaging agent is a SPECT or PET, or magnetic resonance imaging agent; b) imaging the neuronal tissue of the mammal; c) identifying the activated neurons as those neurons which have a significantly increased amount of detectable signal from the detectable moiety compared to the amount of detectable signal from other neurons in the tissue.

As such, in accordance with an embodiment, the present invention provides a method for identifying a neuron or population of neurons as having aberrant or dysregulated NMP function comprising: a) providing at least one first in vitro culture comprising a neuron or population of neurons of interest; b) providing at least one second in vitro normal or control cultures comprising a wild type or standard neuron or population of neurons; c) contacting the neurons of the first and second cultured with a stimulant compound for a period of time sufficient to allow NMP mediated production of SNAPPs into the growth medium; c) providing a negative control in vitro culture comprising a wild type or standard neuron or population of neurons by contacting the neurons of the negative control for a period of time sufficient with a carrier or vehicle which will not stimulate NMP mediated production of SNAPPs into the growth medium; d) removing at least a portion of the growth medium of the cultures of a) to c) and performing an isolation step to purify the SNAPPs from the cultures of a) to c); e) quantifying the amount of SNAPPs isolated in e) from the cultures of a) to c); and f) determining that the first in vitro culture of interest has dysregulated NMP function when the quantity of SNAPPs isolated from a) are significantly increased or decreased when compared with the amount of SNAPPs in b).

BRIEF DESCRIPTION OF THE DRAWINGS

FIGS. 2A-2G show that the Neuronal Membrane Proteasome (NMP) is surface-exposed, neuronal-specific, and temporally regulated. (A) Above, Schematic depicting 20S proteasome composition, as well as approaches taken to evaluate whether membrane proteasomes are exposed to the extracellular space. Both the cytosolic and membrane proteasome are localized to the neuronal soma and dendrites. Below, immunofluorescence images from fixed neurons, either permeabilized (left) or non-permeabilized, (right) are stained using antibodies against proteasomal beta subunits and MAP2. (B,C) Proteasomes are exposed to the extracellular space. (B) Proteinase K (PK) was applied onto cultured cortical neurons for the indicated times. Cytosolic or plasma membrane fractions subjected to immunoblotting for N-terminal antibody against GluR1 (N-GluR1), core alpha proteasome subunits (α1-7), and Tubulin. (C) Biotinylated proteins from surface biotinylated 14 DIV cortical neurons were precipitated on streptavidin affinity beads and subjected to immunoblotting. Inputs are shown to the left of streptavidin pulldown. (D, E) Surface-exposed proteasome expression is unique to nervous system tissues. (D) Streptavidin pulldown (Strep) done from Neuroblastoma-2A (N2A), HEK293 kidney cell lines (HEK), and cortical neurons (Cort). (E) Streptavidin pulldown (Strep) done from tissues dissected from a P3 mouse Cortex (Ctx), Hippocampus (Hip), Olfactory bulb (Olf), Hind Brain (Brn), Heart (Ht), Lung (Lg), Kidney (Kid), Liver (Lv), Pancreas (Pnc). (F) Surface proteasome expression is temporally regulated. Biotinylated proteins from surface biotinylated cortical neurons were precipitated on streptavidin affinity beads and subjected to immunoblotting. Inputs are shown to the left of streptavidin pulldown. Streptavidin pulldown was done at the indicated Days In Vitro (DIV). (G) Schematic shows surface biotinylation done in neuronal cultures at 7 and 8 DIV. Biotinylated proteins were precipitated using streptavidin affinity beads and then analyzed by LC/MS. Core proteasomal subunits expressed at the surface at 8 DIV and not at 7 DIV as shown by mass spectrometry are listed in the table. Molecular weight and % coverage by mass spectrometry shown.

FIGS. 3A-3D show that the NMP mediates degradation of intracellular proteins into extracellular peptides. (A) Representative autoradiograph of lysates from cortical neurons radiolabeled with $^{35}$S methionine/cysteine for 10 minutes in the presence or absence of MG-132. (B) Schematic for collection and purification of extracellular peptides. Media from radiolabeled neurons is collected and purified. Media collected from neurons following radiolabeling was subjected to size exclusion purification, with or without Proteinase K (PK). The percentage of total radioactivity eluting at different sizes is shown. *P<0.01 (two-tailed Student's t-test). Data are presented as mean±SEM (n=3). (C) Rapid efflux of radioactive material out of neuronal cells into media depends upon proteasome function. Media collected from neurons following radiolabeling with or without MG-132 or ATPγS. Liquid scintillation quantification of media at indicated time points is shown normalized to control at the 10 minute time point; 2 minute time point shown separately on the bar graph. Media collected from 14 DIV neurons following radiolabeling without or with MG-132 or ATPγS. *P<0.01 (one-way ANOVA). Data represent mean±SEM (n=3). (D) Release of proteasome-derived peptides in the extracellular space correlates with NMP expression. Experiment performed as described in (C); media collected from either 7 DIV or 8 DIV neurons, with or without MG-132.

DETAILED DESCRIPTION OF THE INVENTION

Figure 1A:
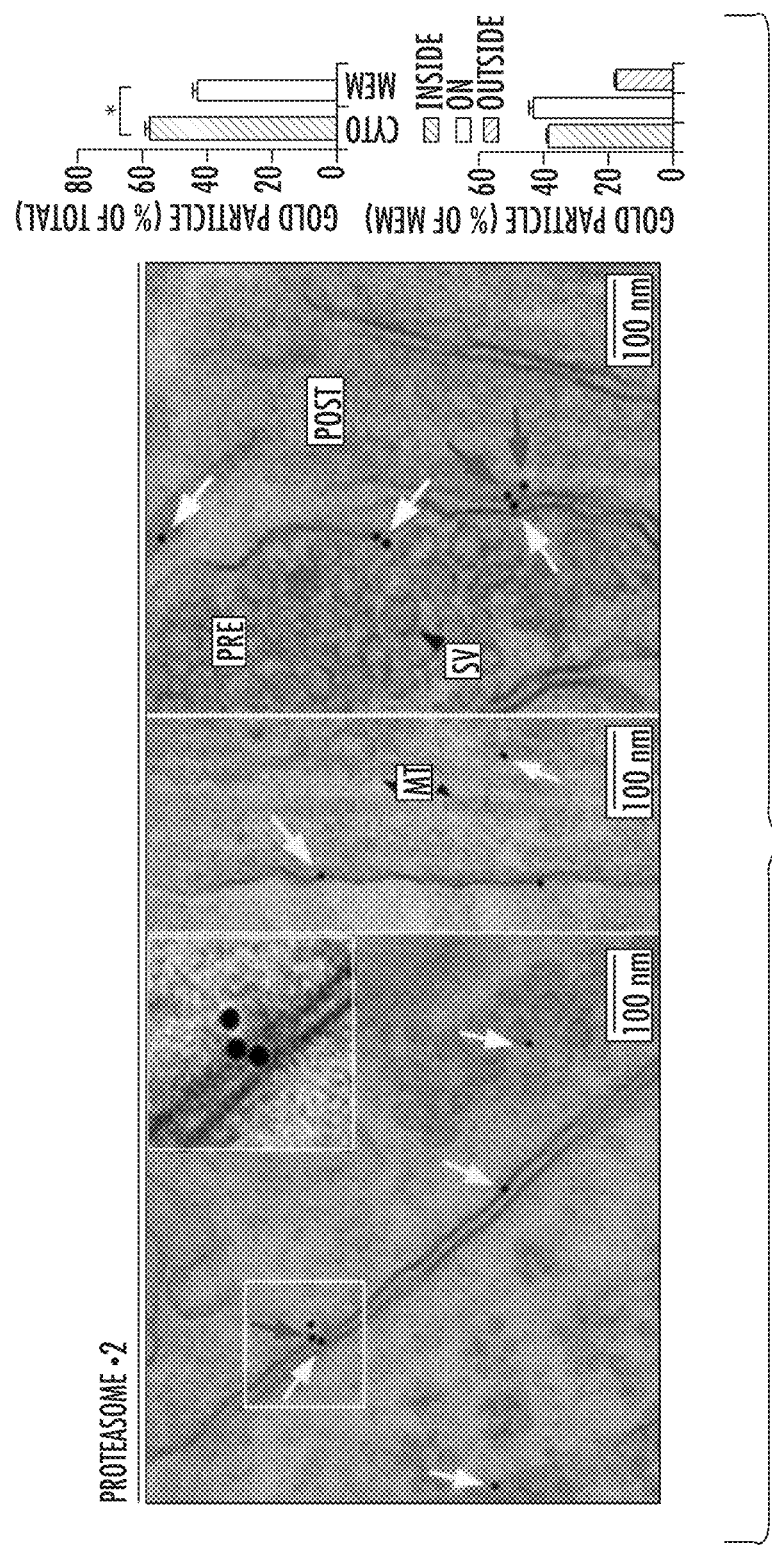
FIGS. 1A-1E show a 20S proteasome is integral to the neuronal plasma membrane and is catalytically active. (A) Immuno-EM of core catalytic β2 proteasomal subunits in cortical neurons, with representative images shown. Inset shows magnified region. Labeled ultrastructures: presynaptic (Pre); postsynaptic (Post); Microtubules (MT); synaptic vesicles (SV). Arrows corresponding to immunogold label; cytosolic (white); membrane (red-cytosolic face), (yellow-directly on), (green-extracellular face). Quantification of shown to right (n=84, >300 gold-particles). *P<0.01 (two-tailed Student's t-test). Data are presented as mean±SEM. (B) Proteasome subunits interact with the plasma membrane. Cortical neurons were fractionated into cytosolic and plasma membrane components. Plasma membranes were extracted with indicated sequentially increasing concentrations of detergent. Samples were analyzed by immunoblotting using antibodies against indicated proteins. Quantification compared cytosolic signal to that of the combined membrane fractions. .*P<0.01 (two-tailed Student's t-test). Data are presented as mean±SEM (n=3). (C) Proteasome subunits fractionate as integral membrane proteins. Western blots of cytosolic, peripheral-membrane (periph.), and integral-membrane (integ.) proteins fractions from cortical neurons. (D,E) Proteasomes at membranes are molecularly distinct, catalytically active, and intact 20S proteasomes. (D) Western blots of purified proteasomes using capped-26S or 20S purification matrices. Purification was done out of either cytosol (Cyt. Pure) or detergent-extracted plasma membranes (Mem. Pure) from cortical neurons. (E) Purified 20S proteasomes from neuronal cytosol or membrane were incubated with the fluorescent proteasome peptide substrate SUC-LLVY-AMC. Endpoint fluorescence is plotted to reflect activity of both 20S and 26S proteasomes. *P<0.01 (two-tailed Student's t-test). Data are presented as mean±SEM (n=3).

Proteasomes are ubiquitously expressed large multisubunit catalytic complexes, generally characterized by a uniform cytoplasmic and nuclear distribution. The present inventors have now identified a nervous system-specific proteasome that is bound to the plasma membrane and exposed to the extracellular space. While it is unclear how these proteasomes bind to and orient themselves within neuronal plasma membranes, it has been known for decades through in vitro studies that proteasomes can orient perpendicularly to membranes specifically enriched in phosphatidylinositol (PI), a key signaling phospholipid that is notably elevated in the nervous system over other tissues.

The data disclosed herein support the idea that the NMP is either part of a protein pore complex at the plasma membrane or itself transmembrane. While the presence of a transmembrane proteasome would have been thought to disrupt the equilibrium neuronal resting membrane potential by exposing the cytosol to the extracellular space, the crystal structure of the uncapped 20S proteasome demonstrates that this complex is gated on both ends and opens only to allow proteins through for degradation. Since the inventors have now found that the NMP is a 20S proteasome complex, it is thought that it would therefore not disrupt the neuronal membrane potential if it were a transmembrane protein.

Based on the studies disclosed herein, the present inventors have surprisingly found a novel degradation machinery in the neurons that mediate neuronal activity-induced degradation of synthesized proteins to produce biologically meaningful peptides. This is, at least in part, mediated through the novel NMP of the present invention in order to produce signaling peptides important for maintaining and enhancing neuronal activity dependent processes.

The present inventors have found that neuronal activity does not simply promote global protein degradation, but rather, it promotes protein degradation exclusively of newly synthesized proteins through the NMP for the express purpose of generating a new class of signaling molecules, SNAPPs.

The SNAPPs generated by the NMP of the present invention are a new modality for neuronal communication. In the release experiments described herein, the inventors can show that there is some peptide release under non-stimulating conditions that is inhibited by MG-132, a known proteasomal inhibitor, and biotin-epoxomicin, a novel NMP specific inhibitor. It is thought that this is due to baseline asynchronous spontaneous network activity causing some baseline degradation of proteins by the NMP, leading to peptides being released into the media. These peptides are a diluted pool of SNAPPs, as they do not possess the same magnitude of signaling capacity as SNAPPs purified from globally stimulated neurons.

Without being held to any particular theory, a possibility is that SNAPPs associate with MHC complexes. Recent studies have identified that MHC complexes play key roles in developmental and experience-dependent mechanisms in the nervous system. It is also possible that SNAPPs interact with other receptors, either known or yet to be identified, or with cell surface lipids. While these inventive studies specifically trace those that are secreted in the media, we recognize that based on the possible mechanism, there may be a variety of SNAPPs that bind immediately to cells due to them being hydrophobic.

Of note in some aspects of the present invention, is the role for phosphorylated CaMKII in NMP expression. This is particularly intriguing given the role for phosphorylated CaMKII in serving as a scaffold for recruiting the proteasome into dendritic spines, and additionally for its long-known and well-studied role in learning and memory.

The same groups that have demonstrated the role for CaMKII in proteasome recruitment to spines have also shown that rapid inhibition of the proteasome has profound effects on synaptic signaling and transmission. These effects range from changes in transmission at the *Drosophila* neuromuscular synapse, regulation of activity-dependent spine dynamics, and an essential role in maintenance of LTP. In accordance with the inventive compositions and methods, we see a similar rapid and acute role for the proteasome in mediating SNAPP release (data not shown). It is important to note that pharmacological inhibitors used in previous studies take a substantially longer time to achieve functional inhibition of the cytosolic proteasome, according to data from groups studying the kinetics of proteasome inhibitors in neurons. Given the present findings, it is thought that at least some of the effects on synaptic transmission and function demonstrated by older studies may be due to inhibition of the neuronal membrane proteasome first reported in this study, and not of the cytosolic proteasome.

In accordance with an embodiment, the present invention provides a method for diagnosing a NMP associated disease or disorder of neuronal cells in a subject comprising: a) obtaining a sample of neuronal tissue from the subject; b) isolating the surface proteins of the neuronal tissue; c) analyzing the surface proteins of b) for the quantity of expression of one or more 20S protein core subunit proteins; d) providing a reference neuronal tissue sample; e) comparing the quantity of expression of one or more 20S protein core subunit proteins from the sample of a) to the quantity of expression of one or more 20S protein core subunit proteins from the reference sample; and f) identifying the subject as having a NMP associated disease or disorder of neuronal cells when the quantity of expression of one or more 20S protein core subunit proteins from the neuronal tissue sample of the subject is significantly greater or less than the quantity of expression of one or more 20S protein core subunit proteins from the reference sample.

As used herein, the term "Neuronal Membrane Proteasome (NMP)" means a neuronal-specific 20S proteasome complex that was expressed at neuronal plasma membranes and exposed to the extracellular space. The NMP is unique to the nervous system and produces SNAPPs into the extracellular space.

As used herein, the analysis of proteins which are located on the plasma membrane surface of the neuronal cell, can be performed using many different means known in the art. In an embodiment, the plasma membrane fraction is isolated from neurons by lysing them in either a sucrose buffer or hypotonic lysis buffer. Nuclei were pelleted, and the supernatant containing plasma membranes was then pelleted at high RPM. Once the supernatant (cytosolic fraction) was set aside, the pellet was washed 2× with lysis buffer, and then resuspended in lysis buffer with indicated concentrations of detergent. Following a 15-minute incubation in the buffer, samples were spun down. This was repeated for all indicated concentrations of detergent. Membrane association was determined by classic methods of sodium carbonate extraction. The proteins were visualized by SDS-PAGE methods. Other methods can be used.

As used herein the 20S core proteins associated with the NMP can be identified and analyzed through the use of an antibodies that detect $\beta 2$, anti-$\alpha 1$-7 proteasome subunit, anti-$\alpha 5$ proteasome subunit, anti-$\beta 1$ proteasome subunit, anti-$\beta 2,5$ subunit, anti-$\beta 2$ proteasome subunit, and anti-Rpt5 proteasome subunit, for example. Other method for identification are known in the art, and include, for example, surface biotinylation methods and mass spectrometry.

In accordance with an embodiment, the present invention provides a method for diagnosing degenerative disease or disorder of central nervous system neuronal cells in a subject comprising: a) obtaining a biological sample from said human subject; a) obtaining a sample of neuronal tissue from the subject; b) isolating the surface proteins of the neuronal tissue; c) analyzing the surface proteins of b) for the quantity of expression of one or more 20S protein core subunit proteins; d) providing a reference neuronal tissue sample; e) comparing the quantity of expression of one or more 20S protein core subunit proteins from the sample of a) to the quantity of expression of one or more 20S protein core subunit proteins from the reference sample; and f) identifying the subject as having a degenerative disease or disorder of neuronal cells when the quantity of expression of one or more 20S protein core subunit proteins from the neuronal tissue sample of the subject is significantly less than the quantity of expression of one or more 20S protein core subunit proteins from the reference sample.

In accordance with another embodiment, the present invention provides a method for identifying a human subject as having a NMP associated disease or disorder of neuronal cells comprising: a) obtaining a biological sample from said human subject; b) quantifying the amount of SNAPPs in the sample from a); c) comparing the amount of SNAPPs in the sample from a) to the amount of SNAPPs in samples from normal control subjects; and d) identifying the subject as having a NMP associated disease or disorder of neuronal cells when the quantity of SNAPPs in the sample from a) is significantly greater or less than the quantity of SNAPPs in samples from normal control subjects.

In accordance with an embodiment, the present invention provides a composition comprising one or more SNAPPs.

In accordance with an embodiment, the present invention provides a composition comprising one or more SNAPPs and at least one agent, detectable moiety or biologically active agent.

As used herein, the term "SNAPP" means proteins and peptides which are secreted extracellularly by a novel neural membrane bound proteasome (NMP) as the result of neural stimulation. Typically, these SNAPPs are secreted extracellularly within a few seconds to minutes after neural stimulation. These SNAPPs range in size from about 500 Daltons to about 3000 Daltons.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and unnatural amino acids. Many types of amino acid residues are useful in the adipokine polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

The term, "peptide," or "oligopeptide," as used herein, includes a sequence of from four to sixteen amino acid residues in which the α-carboxyl group of one amino acid is joined by an amide bond to the main chain (α- or β-) amino group of the adjacent amino acid. In some embodiments, peptides provided herein for use in the described and claimed methods and compositions can be cyclic.

The term "imaging agent," is known in the art. As used herein, the one or more imaging agents can be any small molecule or radionuclide which is capable of being detected. In accordance with some embodiments the imaging agent is a fluorescent dye. The dyes may be emitters in the visible or near-infrared (NIR) spectrum. Known dyes useful in the present invention include carbocyanine, indocarbocyanine, oxacarbocyanine, thüicarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Organic dyes which are active in the NIR region are known in biomedical applications. However, there are only a few NIR dyes that are readily available due to the limitations of conventional dyes, such as poor hydrophilicity and photostability, low quantum yield, insufficient stability and low detection sensitivity in biological system, etc. Significant progress has been made on the recent development of NIR dyes (including cyanine dyes, squaraine, phthalocyanines, porphyrin derivatives and BODIPY (borondipyrromethane) analogues) with much improved chemical and photostability, high fluorescence intensity and long fluorescent life. Examples of NIR dyes include cyanine dyes (also called as polymethine cyanine dyes) are small organic molecules with two aromatic nitrogen-containing heterocycles linked by a polymethine bridge and include Cy5, Cy5.5, Cy7 and their derivatives. Squaraines (often called Squarylium dyes) consist of an oxocyclobutenolate core with aromatic or heterocyclic components at both ends of the molecules, an example is KSQ-4-H. Phthalocyanines, are two-dimensional 18π-electron aromatic porphyrin derivatives, consisting of four bridged pyrrole subunits linked together through nitrogen atoms. BODIPY (boron-dipyrromethane) dyes have a general structure of 4,4'-difluoro-4-bora-3a, 4a-diaza-s-indacene) and sharp fluorescence with high quantum yield and excellent thermal and photochemical stability.

Other imaging agents which can be attached to the SNAPPs of the present invention include PET and SPECT imaging agents. The most widely used agents include branched chelating agents such as di-ethylene tri-amine penta-acetic acid (DTPA), 1,4,7,10-tetra-azacyclododecane-1,4,7,10-tetraacetic acid (DOTA) and their analogs. Chelating agents, such as di-amine dithiols, activated mercaptoacetyl-glycyl-glycyl-gylcine (MAG3), and hydrazidonicotinamide (HYNIC), are able to chelate metals like $^{99m}$Tc and $^{186}$Re. Instead of using chelating agents, a prosthetic group such as N-succinimidyl-4-$^{18}$F-fluorobenzoate ($^{18}$F-SFB) is necessary for labeling peptides with $^{18}$F. In accordance with a preferred embodiment, the chelating agent is DOTA.

In accordance with some embodiments, the present invention provides one or more SNAPPs wherein the imaging agent comprises a metal isotope suitable for imaging. Examples of isotopes useful in the present invention include Tc-94m, Tc-99m, In-111, Ga-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, or Dy-i66.

In accordance with some embodiments, the present invention provides a SNAPP wherein the reporter portion comprises $^{111}$In labeled DOTA which is known to be suitable for use in SPECT imaging.

In accordance with an embodiment, the present invention provides a method for identifying and targeting activated neurons in vivo using the ability of SNAPPs to bind to activated neurons to target a conjugated molecule to activated neurons, comprising: a) administering to the neuronal tissue of a mammal an effective amount of at least one or more SNAPP compositions as described herein, wherein the imaging agent is a SPECT or PET, or magnetic resonance imaging agent; b) imaging the neuronal tissue of the mammal; c) identifying the activated neurons as those neurons which have a significantly increased amount of detectable signal from the detectable moiety compared to the amount of detectable signal from other neurons in the tissue.

In accordance with some other embodiments, the present invention provides SNAPPs wherein the imaging agent comprises $Gd^{3+}$ labeled DOTA which is known to be suitable for use in MR imaging. It is understood by those of ordinary skill in the art that other suitable radioisotopes can be substituted for $^{111}In$ and $Gd^{3+}$ disclosed herein.

In accordance with some embodiments, the present invention provides SNAPPs with wherein the at least one detectable moiety is a mass spectra agent for enhancing or modifying mass spectra, such as coumarin, or any derivitzation procedure such as 4-sulfophenyl isothiocyanate (SPITC), Edman's reagent, N-terminal modifications such as Quaternary Ammonium derivatives like methyl iodide to generate trimethylammonium derivatives, Quarternary Phosphonium derivatives like 2-bromoethyl-triphenylphosphonium bromide, molecules that contain High Proton Affinities such as dansyl chloride, C-terminal derivatives such as 1-(3-dimethylaminopropyl)-3-ethylcarbodiimide (EDC), side-chain derivatives such as 2,4,6-trimethyl pyridinium, or negative charged derivatives such as pentafluorobenzoyl fluoride that allows for easier characterization of mass spectra.

In some embodiments, the present invention provides methods for detecting neuronal activity using voltage-sensitive dye, whose optical properties change during changes in electrical activity of neuronal cells. The spatial resolution achieved by this technique is near the single cell level. For example, researchers have used the voltage-sensitive dye merocyanine oxazolone to map cortical function in a monkey model. Blasdel, G. G. and Salama, G., "Voltage Sensitive Dyes Reveal a Modular Organization Monkey Striate Cortex," Nature 321:579-585, 1986. However, the use of these kinds of dyes would pose too great a risk for use in vivo in view of their toxicity.

It will be understood by those of ordinary skill in the art that the SNAPPs of the present invention have the ability to bind activated neurons, and therefore they can be used as targeting molecules for other therapies. For example, SNAPPs can be conjugated with another small molecule, or biologically active agent, including, drugs, antibodies and the like. In accordance with some embodiments, the SNAPPs can be conjugated or linked with compounds which stimulate or inhibit neuronal activity, or which have some other pharmacological effect.

As used herein, the term "biologically active agent" include any compound, biologics for treating brain-related diseases, e.g. drugs, inhibitors, and proteins. An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc.

Examples of such classes of compounds include, but are not limited to, cholinergic agonists and antagonists, opiate agonists and antagonists, muscarinic agonists and antagonists, GABAergic agonists and antagonists, parasympathomimetics, sympathomimetics, adrenergic agonists and antagonists, general anesthetics, such as inhalation anesthetics, halogenated inhalation anesthetics, intravenous anesthetics, barbiturates, benzodiazepines, antidepressants, heterocyclic antidepressants, monoamine oxidase inhibitors selective serotonin re-uptake inhibitors tricyclic antidepressants, antimanics, anti-psychotics, phenothiazine antipsychotics, anxiolytics, calcium channel blockers, and anti-Parkinson's agents such as bromocriptine, levodopa, carbidopa, and pergolide.

It is understood by those of ordinary skill in the art that the imaging agents can be attached to the SNAPPs by use of a linker molecule. For instance linking groups having alkyl, aryl, combination of alkyl and aryl, or alkyl and aryl groups having heteroatoms may be present. For example, the linker can be a $C_1$-$C_{20}$ alkyl, $C_2$-$C_{20}$ alkenyl, $C_2$-$C_{20}$ alkynyl, $C_1$-$C_{20}$ hydroxyalkyl, $C_1$-$C_{20}$ alkoxy, $C_1$-$C_{20}$ alkoxy $C_1$-$C_{20}$ alkyl, $C_1$-$C_{20}$ alkylamino, di-$C_1$-$C_{20}$ alkylamino, $C_1$-$C_{20}$ dialkylamino $C_1$-$C_{20}$ alkyl, $C_1$-$C_{20}$ thioalkyl, $C_2$-$C_{20}$ thioalkenyl, $C_2$-$C_{20}$ thioalkynyl, $C_6$-$C_{22}$ aryloxy, $C_6$-$C_{22}$ acylamino $C_2$-$C_{20}$ acyloxy, $C_2$-$C_{20}$ thioacyl, $C_1$-$C_{20}$ amido, and $C_1$-$C_{20}$ sulphonamido.

Compounds are assembled by reactions between different components, to form linkages such as ureas (—NRC(O)NR—), thioureas (—NRC(S)NR—), amides (—C(O)NR— or —NRC(O)—), or esters (—C(O)O— or —OC(O)—). Urea linkages may be readily prepared by reaction between an amine and an isocyanate, or between an amine and an activated carbonamide (—NRC(O)—). Thioureas may be readily prepared from reaction of an amine with an isothiocyanate. Amides (—C(O)NR— or —NRC(O)—) may be readily prepared by reactions between amines and activated carboxylic acids or esters, such as an acyl halide or N-hydroxysuccinimide ester. Carboxylic acids may also be activated in situ, for example, with a coupling reagent, such as a carbodiimide, or carbonyldiimidazole (CDI). Esters may be formed by reaction between alcohols and activated carboxylic acids. Triazoles are readily prepared by reaction between an azide and an alkyne, optionally in the presence of a copper (Cu) catalyst.

Protecting groups may be used, if necessary, to protect reactive groups while the compounds are being assembled. Suitable protecting groups, and their removal, will be readily available to one of ordinary skill in the art.

In this way, the compounds may be easily prepared from individual building blocks, such as amines, carboxylic acids, and amino acids.

It is contemplated that any of the SNAPPs of the present invention described above can also encompass a pharmaceutical composition comprising the SNAPPs and a pharmaceutically acceptable carrier.

In accordance with another embodiment, the present invention provides a method for identifying and targeting activated neurons in vitro comprising: a) providing a plurality of in vitro cultures comprising a plurality of neurons in a growth medium; b) stimulating at least one or more of the cultures with a stimulant; c) removing the growth medium of the plurality of in vitro cultures; d) fixing the plurality of in vitro cultures; e) staining the plurality of in vitro cultures with at least one or more SNAPP compositions as described herein; f) quantifying the detectable moiety of the compositions of e) using imaging and/or radiography; g) identifying the activated neurons as those neurons from stimulated in vitro cultures which have a significantly increased amount of detectable signal from the detectable moiety compared to the amount of detectable signal in neurons from in vitro cultures which were not stimulated; and h) using the ability of SNAPPs to bind to activated neurons to target a conjugated molecule to activated neurons.

With respect to the SNAPPs described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular SNAPP composition, as well as by the particular method used to administer the composition. Accordingly, there are a variety of suitable formulations of the pharmaceutical SNAPP composition of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, PA, Banker and Chalmers, eds., pages 238-250 (1982), and *ASHP Handbook on Injectable Drugs*, Trissel, 15th ed., pages 622-630 (2009)).

For purposes of the invention, the amount or dose of the SNAPPs of the present invention that is administered should be sufficient to effectively target the cell, or population of cells in vivo, such that the stimulation of the neuronal cells can be detected, in the subject over a reasonable time frame. The dose will be determined by the efficacy of the particular SNAPP formulation and the location of the target population of neuronal cells in the subject, as well as the body weight of the subject to be treated.

The dose of the SNAPPs of the present invention also will be determined by the existence, nature and extent of any adverse side effects that might accompany the administration of a particular SNAPP. Typically, an attending physician will decide the dosage of the SNAPPs with which to treat each individual subject, taking into consideration a variety of factors, such as age, body weight, general health, diet, sex, compound to be administered, route of administration, and the severity of the condition being treated. By way of example, and not intending to limit the invention, the dose of the SNAPPs of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the SNAPPs of the present invention can be at a concentration from about 1 nM to about 10,000 nM, preferably from about 10 nM to about 5,000 nM, more preferably from about 100 nM to about 500 nM.

In accordance with another embodiment, the present invention provides a method for identifying activated neurons in vitro comprising: a) providing a plurality of in vitro cultures comprising a plurality of neurons in a growth medium; b) stimulating at least one or more of the cultures with a stimulant; c) removing the growth medium of the plurality of in vitro cultures; d) fixing the plurality of in vitro cultures; e) staining the plurality of in vitro cultures with at least one or more SNAPP compositions as described herein; f) quantifying the detectable moiety of the compositions of e) using imaging and/or radiography; g) identifying the activated neurons as those neurons from stimulated in vitro cultures which have a significantly increased amount of detectable signal from the detectable moiety compared to the amount of detectable signal in neurons from in vitro cultures which were not stimulated.

In accordance with a further embodiment, the present invention provides a method for screening for compounds which stimulate NMP and subsequent production of secreted cortical neuronal-activity induced proteasomal peptides (SNAPPs) comprising the steps of: a) administering to a subject a test compound for a period of time sufficient to stimulate NMP and allow production of SNAPPs in the neurons of the subject; b) providing a negative control by administering to at least a second subject for a period of time sufficient with a carrier or vehicle which will not stimulate NMP mediated production of SNAPPs in the neurons of the second subject; c) obtaining a biological sample from a) and b) and performing an isolation step to purify the SNAPPs from the biological samples of b) and c); d) quantifying the amount of SNAPPs isolated in e) from the biological samples of a) and b); and e) determining that the test compound is a stimulator of NMP mediated SNAPP production when the quantity of SNAPPs isolated from the biological samples of a) are significantly increased when compared with the amount of SNAPPs isolated from the biological samples of b).

In accordance with another embodiment, the present invention provides a method for screening for compounds which inhibit NMP mediated production of secreted neuronal-activity induced proteasomal peptides (SNAPPs) in a subject comprising the steps of: a) administering to a first subject a test compound thought to be an inhibitor of NMP for a period of time sufficient to allow NMP mediated production of SNAPPs in the subject; b) providing a negative control by administering to at least a second subject for a period of time sufficient with a carrier or vehicle which will not stimulate NMP and secretion of SNAPPs in the second subject; c) providing a positive control by administering to at least a third subject for a period of time sufficient with a known neuronal stimulant to allow NMP mediated production of SNAPPs in the subject; d) obtaining biological samples from the subjects of a) to c) and performing an isolation step to purify the SNAPPs from the biological samples of a) to c); e) quantifying the amount of SNAPPs isolated in d) from the biological samples of a) to c); and f) determining that the test compound is an inhibitor of NMP mediated SNAPP production when the quantity of SNAPPs isolated from the biological samples of a) are significantly reduced when compared with the amount of SNAPPs isolated from the biological samples of b) and/or c).

In accordance with another embodiment, the present invention provides a method for identifying activated neurons in vivo comprising: a) administering to the neuronal tissue of a mammal an effective amount of at least one or more SNAPP compositions as described herein, wherein the imaging agent is a SPECT or PET, or magnetic resonance imaging agent; b) imaging the neuronal tissue of the mammal; and c) identifying the activated neurons as those neurons which have a significantly increased amount of detectable signal from the detectable moiety compared to the amount of detectable signal from other neurons in the tissue.

In some embodiments the present invention employs an electromagnetic radiation (emr) source for uniformly illuminating an area of neurons of interest, and an optical detector capable of detecting and acquiring data relating to one or more optical properties of an area of interest. In a simple form, the apparatus of the present invention may include an optical fiber operably connected to an emr source that illuminates tissue or neuronal cultures in vitro, and another optical fiber operably connected to an optical detector, such as a photodiode, that detects one or more optical properties of the illuminated tissue. The detector is used to obtain control data representing the "normal" or "background" optical properties of an area of interest, and then to obtain subsequent data representing the optical properties of an area of interest during neuronal activity, e.g., stimulation of neuronal tissue, or during a monitoring interval. The subsequent data is compared to the control data to identify changes in optical properties representative of neuronal activity. According to a preferred embodiment, the control, subsequent and comparison data are presented in a visual format as images.

In some embodiments, the present invention provides methods for optically imaging neuronal tissue and the physiological events associated with neuronal activity. The methods of the present invention may be used for optically imaging and mapping functional neuronal activity, differentiating neuronal tissue from non-neuronal tissue, identifying and spatially locating dysfunctional neuronal tissue, and monitoring neuronal tissue to assess viability, function and the like.

Numerous devices for acquiring, processing and displaying data representative of one or more optical properties of an area of interest can be employed. One preferred device is a video camera that acquires control and subsequent images of an area of interest that can be compared to identify areas of neuronal activity or dysfunction. Examination of images provides precise spatial location of areas of neuronal activity or dysfunction. Apparatus suitable for obtaining such images have been described in the patents incorporated herein by reference and are more fully described below. For most surgical and diagnostic uses, the optical detector preferably provides images having a high degree of spatial resolution at a magnification sufficient to detect single neuronal cells or nerve fiber bundles. Several images are preferably acquired over a predetermined time period and combined, such as by averaging, to provide control and subsequent images for comparison.

In some embodiments the video camera is a Charge Coupled Device (CCD). A CCD is a type of optical detector that utilizes a photo-sensitive silicon chip in place of a pickup tube in a video camera.

Various data processing techniques may be advantageously used to assess the data collected in accordance with the present invention. Comparison data may be assessed or presented in a variety of formats. Processing may include averaging or otherwise combining a plurality of data sets to produce control, subsequent or comparison data sets. Images are preferably converted from an analog to a digital form for processing, and back to an analog form for display.

Data processing may also include amplification of certain signals or portions of a data set (e.g., areas of an image) to enhance the contrast seen in data set comparisons, and to thereby identify areas of neuronal activity and/or dysfunction with a high degree of spatial resolution. For example, according to one embodiment, images are processed using a transformation in which image pixel brightness values are remapped to cover a broader dynamic range of values. A "low" value may be selected and mapped to zero, with all pixel brightness values at or below the low value set to zero, and a "high" value may be selected and mapped to a selected value, with all pixel brightness values at or above the high value mapped to the high value. Pixels having an intermediate brightness value, representing the dynamic changes in brightness indicative of neuronal activity, may be mapped to linearly or logarithmically increasing brightness values. This type of processing manipulation is frequently referred to as a "histogram stretch" and can be used according to the present invention to enhance the contrast of data sets, such as images, representing changes in neuronal activity.

In accordance with another embodiment, the present invention provides a method for making SNAPPs comprising the steps of: a) providing an in vitro culture of a plurality of neurons in a growth medium; b) stimulating the neurons for a period of time sufficient to allow secretion of SNAPPs into the growth medium; c) removing at least a portion of the growth medium containing the SNAPPs.

The term "neuron" is used herein to denote a cell that arises from neuroepithelial cell precursors. Mature neurons (i.e., fully differentiated cells from an adult) display several specific antigenic markers.

The term "neuroepithelium" is used herein to denote cells and tissues that arise from the neural epithelium during development; such cells include retinal cells, diencephalon cells and midbrain cells. Neuroepithelium is also defined as neuroectoderm, and more specifically as ectoderm on the dorsal surface of the early vertebrate embryo that gives rise to the cells (neurons and glia) of the nervous system.

As used herein, the term "neuron" means neuronal cells derived from the central nervous system of a subject, including, for example, the brain, spinal cord, as well as the peripheral nervous system, including, for example, sensory and motor neurons. Areas of the brain where these neurons can originate from include, but are not limited to, Cortex (Ctx), Hippocampus (Hip), Olfactory bulb (Olf), Hind Brain (Brn), for example. Neurons can also be cells derived from induced pluripotent stem cell (iPSC) cultures.

The cell culture systems and methods used in the present invention may be used in conjunction with any glass surface (including, for instance, coverslips) that has been coated with an attachment-enhancing substance, such as polylysine, Matrigel, laminin, polyornithine, gelatin and/or fibronectin. Feeder cell layers, such as glial feeder layers or embryonic fibroblast feeder layers, may also find use within the methods and compositions provided herein.

Neuronal cells used in the present invention can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of Neurobasal and B-27 (catalog #21103049 and 17504044 respectively, Life Technologies, Gaithersburg, MD).

Conditions for culturing should be close to physiological conditions. The pH of the culture media should be close to physiological pH, preferably between pH 6-8, more preferably close to pH 7, even more particularly about pH 7.4. Cells should be cultured at a temperature close to physiological temperature, preferably between 30° C.-40° C., more preferably between 32° C.-38° C., and most preferably between 35° C.-37° C.

Neuronal cells can be grown in suspension or on a fixed substrate. In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3-4 days in a 37° C. incubator, and proliferation can be reinitiated at any time after that by dissociation of the cells and resuspension in fresh medium containing growth factors.

As used herein, the term "stimulation" means the activation or firing of the neuron when the neuron is stimulated by pressure, heat, light, or chemical information from other cells. The type of stimulation necessary to produce firing depends on the type of neuron. The cytosol inside a neuron is separated from that outside by a polarized cell membrane that contains electrically charged particles known as ions. When a neuron is sufficiently stimulated to reach the neural threshold (a level of stimulation below which the cell does not fire), depolarization, or a change in cell potential, occurs.

In accordance with some embodiments, neurons which produce SNAPPs can be stimulated by the use of a depolarizing buffer. Examples of such buffers include, but are not limited to physiological buffers containing high concentration of KCl (60 mM to 150 mM or more), and can also include additional $Ca^{++}$ ions (10-20 mM). Other such depolarizing buffers include glutamate or bicuculine and others.

Removal of cell growth medium from cell cultures which have been stimulated can be performed using any known means in the art, e.g., pipetting, filtration, etc.

In accordance with an embodiment, the present invention provides a method for inhibiting NMP mediated production of SNAPPs in a neuronal cell or population of cells comprising contacting the cell or population of cells with an effective amount of at least one proteasomal inhibitor for a time sufficient to inhibit the NMP and production of SNAPPs.

In some embodiments, the proteasomal inhibitor can be one known in the art. For example, compounds such as Epoxomicin, biotin-Epoxomicin, Lactacystin, Bortezomib, MG-132, Carfilzomib, MLN9708, Ixazomib, PI-1840, ONX-0914, Oprozomib, CEP-18770, and Gabexate Mesylate are known proteasomal inhibitors.

In accordance with a further embodiment, the present invention provides a method for screening for compounds which stimulate the NMP and thus production of secreted neuronal-activity induced proteasomal peptides (SNAPPs) comprising the steps of: a) providing a plurality of in vitro cultures comprising a plurality of neurons in a growth medium; b) providing one or more test cultures by contacting the neurons of at least a first culture with a test compound for a period of time sufficient to inhibit the NMP and allow production of SNAPPs into the growth medium; c) providing a negative control by contacting the neurons of at least a second culture for a period of time sufficient with a carrier or vehicle which will not stimulate NMP mediated production of SNAPPs into the growth medium; d) removing at least a portion of the growth medium of the cultures of b) and c) and performing an isolation step to purify the SNAPPs from the cultures of b) and c); e) quantifying the amount of SNAPPs isolated in e) from the cultures of b) and c); and f) determining that the test compound is a stimulator of SNAPP secretion when the quantity of SNAPPs isolated from b) are significantly increased when compared with the amount of SNAPPs in c).

In accordance with yet another embodiment, the present invention provides a method for screening for compounds which inhibit the NMP and thus production of secreted neuronal-activity induced proteasomal peptides (SNAPPs) comprising the steps of: a) providing a plurality of in vitro cultures comprising a plurality of neurons in a growth medium; b) providing one or more test cultures by contacting the neurons of at least a first culture with a test compound and with a known neuronal stimulant for a period of time sufficient to allow NMP mediated production of SNAPPs into the growth medium; c) providing a negative control by contacting the neurons of at least a second culture for a period of time sufficient with a carrier or vehicle which will not stimulate NMP mediated production of SNAPPs into the growth medium; d) providing a positive control by stimulating the neurons of a third culture for a period of time sufficient with a known neuronal stimulant to allow secretion of SNAPPs into the growth medium; e) removing at least a portion of the growth medium of the cultures of b) to d) and performing an isolation step to purify the SNAPPs from the cultures of b) to d); f) quantifying the amount of SNAPPs isolated in e) from the cultures of b) to d); and g) determining that the test compound is an inhibitor of SNAPP secretion when the quantity of SNAPPs isolated from b) are significantly reduced when compared with the amount of SNAPPs in c) and/or d).

The isolation and quantification of SNAPPs can be performed by various methods in the art. In some embodiments the SNAPPs can be isolated various chromatographic methods, including, for example, UHPLC Hydrophilic Interaction Chromatography (HILIC), normal phase, and/or reverse-phase C18 chromatography. These methods can be combined with ultraviolet-visible (UV-vis) spectrophotometry, and other detection methods, to detect the SNAPPs eluting at various times off the different columns.

In accordance with some embodiments, the sequences of SNAPPs can be identified with many known methods. In an embodiment, advanced mass spectrometric techniques after fractionation using matrix assisted laser desorption/ionization after HPLC (LC-MALDI) or fractionation of an HPLC column directly into an electrospray mass spectrometer (LC/MS-ESI) can be used to identify the specific SNAPPs. Other methods, such as Edman degradation and sequencing can be used.

Figure 8:
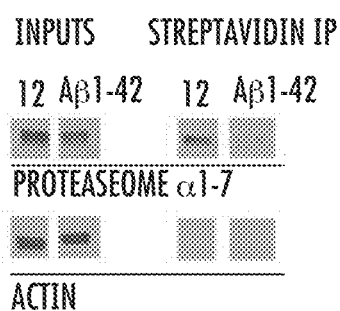
FIG. 8 shows that Dysregulation of the NMP in Alzheimer's disease. NMP expression in mouse cortical neurons treated with a variety of compounds, including Aβ1-42. DIV12 mouse neurons were treated with 1 µM Aβ1-42 peptide for 12 hours. Following treatment, neurons were surface biotinylated, and surface proteins were isolated and analyzed by western blot. Inputs are shown to the left of the streptavidin pulldown. Note the significant change in expression of proteasome subunits in the streptavidin pulldown from Aβ treated neurons.

Considering that many neurodegenerative disorders may result from improperly degraded proteins, we have tested whether the NMP is at all dysregulated in mouse models for neurodegeneration. Interestingly, in accordance with some aspects of the present invention, the inventors found that the NMP is significantly perturbed rapidly in a disease model of Alzheimer's and in human AD brains (FIG. 8) when compared to normal brains.

As such, in accordance with an embodiment, the present invention provides a method for identifying a neuron or population of neurons as having aberrant or dysregulated NMP function comprising: a) providing at least one first in vitro culture comprising a neuron or population of neurons of interest; b) providing at least one second in vitro normal or control cultures comprising a wild type or standard neuron or population of neurons; c) contacting the neurons of the first and second cultured with a stimulant compound for a period of time sufficient to allow NMP mediated production of SNAPPs into the growth medium; c) providing a negative control in vitro culture comprising a wild type or standard neuron or population of neurons by contacting the neurons of the negative control for a period of time sufficient with a carrier or vehicle which will not stimulate secretion of SNAPPs into the growth medium; d) removing at least a portion of the growth medium of the cultures of a) to c) and performing an isolation step to purify the SNAPPs from the cultures of a) to c); e) quantifying the amount of SNAPPs isolated in e) from the cultures of a) to c); and f) determining that the first in vitro culture of interest has dysregulated NMP function when the quantity of SNAPPs isolated from a) are significantly increased or decreased when compared with the amount of SNAPPs in b).

In some embodiments, the above methods can be performed using cysteine or methionine amino acids labeled with $^{35}S$ added to the culture medium prior to performing the methods of the present invention. Other labeled amino acids known in the art can also be used.

For example, the above methods can be used to compare the NMP function of neurons having known neurodegenerative diseases or models for such diseases to normal neuronal function to determine which neurological diseases or conditions are associated with dysregulated or aberrant NMP function.

In accordance with another embodiment, the present invention provides a method for diagnosing a NMP associated disease or disorder of neuronal cells in a subject comprising: a) administering to the subject an effective amount of a NMP stimulator or inhibitor to the subject; b) stimulating the neurons of interest; c) quantifying the amount of SNAPPs released after stimulation; d) comparing the amount of SNAPPs released in the subject to the amount released in normal control subjects; and e) identifying the subject as having a NMP associated disease or disorder of neuronal cells when the quantity of SNAPPs released in the subject in c) is significantly different than the quantity of SNAPPs released in normal control subjects.

Examples of proteasomal stimulators useful in the inventive methods can include, but are not limited to, PA28, PA200, PA700, arginine-rich histone H3), small molecules (oleuropein, betulinic acid—and derivtives), lipid activators (lysophosphatidylinositol, cardiolipin, ceramides), fatty acids (linoleic, oleic, linolenic acids), synthetic peptidyl alcholos (pnitroanilides, nitriles). (Curr Med Chem. 2009; 16(8):931-939).

Figure 7:
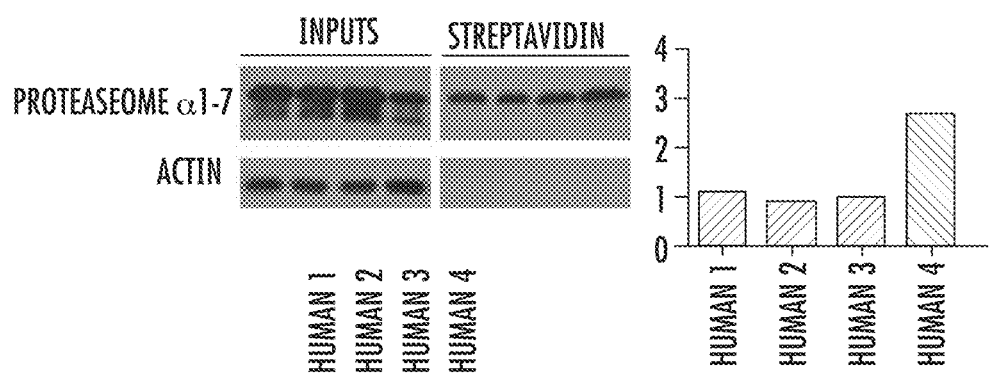
FIG. 7 shows that the NMP expression is conserved in humans and varies across individuals. Fetal human brains were obtained according to Institutional Review Board Protocol. Fresh tissue was dissected and sliced and then surface biotinylated. Surface proteins were isolated on streptavidin beads and subsequently analyzed by western blot. Proteasome subunits were pulled down on streptavidin beads, whereas cytosolic protein actin was not. Inputs are shown to the left of the streptavidin pulldown. Expression is fairly consistent across humans, except for one sample that demonstrated much higher expression. Further analysis revealed that the patient who consented for the procedure was on regular methadone use for treatment of heroin addiction. These samples were run blinded. Densitometry quantification is shown to the right, with expression of the NMP normalized to the total amount of proteasome.

As seen in FIG. 7, it is thought that certain neurological diseases can be caused in whole or in part, by dysregulation of the NMP in the neuronal cells. Certain disorders may in fact, be caused by disruption of NMP function or under expression of NMP proteins, causing an decrease in SNAPP production which may cause under stimulation of neural pathways downstream from the affected cells. Conversely, certain disorders may in fact, be caused by an excess of NMP function or over expression of NMP proteins, causing an increase in SNAPP production which may cause over stimulation of neural pathways downstream from the affected cells, and which may lead to neuronal apoptosis and death. Examples of degenerative diseases of the nervous system and brain which may be affected by changes in NMP function or levels of expression or signaling include, but are not limited to psychiatric disorders, epilepsy, multiple sclerosis, autism, Alzheimer's disease, Parkinson's disease, amyotrophic lateral sclerosis, Huntington's, aging, dementia, enhancement learning and memory and other neurodegenerative diseases.

In accordance with an embodiment, the present invention provides A method for identifying a human subject as having a NMP associated disease or disorder of neuronal cells comprising: a) obtaining a biological sample from said human subject; b) quantifying the amount of SNAPPs in the sample from a); c) comparing the amount of SNAPPs in the sample from a) to the amount of SNAPPs in samples from normal control subjects; and d) identifying the subject as having a NMP associated disease or disorder of neuronal cells when the quantity of SNAPPs in the sample from a) is significantly different than the quantity of SNAPPs in samples from normal control subjects. It will be understood by those of ordinary skill in the art that the quantification of SNAPPs in the sample can be performed using known methods, including, for example, those described here.

As used herein, the term "sample" or "biological sample" means samples that may be derived from bodily fluids, including, for example, one or more selected from blood, serum, plasma, lymph, cerebrospinal fluid (CSF), tears, urine, amniotic fluid, and saliva of the subject being tested, as well as purified extracellular vesicles (EVs) and induced pluripotent stem cells.

In some embodiments, the NMP stimulators or inhibitors are combined with a pharmaceutically acceptable carrier as described herein. Moreover, the proteasomal stimulators or inhibitors can be combined with other biologically active agents.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject.

Examples of active agents that can be used with, or conjugated to the inventive SNAPPs, and NMP stimulators or inhibitors, and methods include, but are not limited to autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, sympatholytics, sympathomimetics, and adrenergic agonist sympathomimetics, anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists, psychotropic agents, such as antidepressants, heterocyclic antidepressants, monoamine oxidase inhibitors selective serotonin re-uptake inhibitors tricyclic antidepressants, antimanics, anti-psychotics, phenothiazine antipsychotics, anxiolytics, sedatives, and hypnotics, barbiturate sedatives and hypnotics, benzodiazepine anxiolytics, sedatives, and hypnotics, and psychostimulants.

In another embodiment, the term "administering" means that at least one or more SNAPPs or NMP stimulators or inhibitors of the present invention are introduced into a subject, preferably a subject receiving treatment for a disease, and the at least one or more SNAPPs or NMP stimulators or inhibitors are allowed to come in contact with the one or more disease related cells or population of cells in vivo.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. Moreover, the term "subject" includes tissues from deceased or fixed tissue.

EXAMPLES

Antibodies.

The following antibodies are commercially available and were used according to manufacturer's suggestions for western blotting and immunocytochemistry: anti-pCreb (Cell Signaling), anti-α1-7 proteasome subunit (Santa Cruz), anti-α5 proteasome subunit (Santa Cruz), anti-β1 proteasome subunit (Santa Cruz), anti-β2,5 subunit (Abcam), anti-β2 proteasome subunit (Santa Cruz), anti-Rpt5 proteasome subunit (Enzo Life Sciences), anti-calregulin (Santa Cruz), anti-S6 (Cell Signaling), anti-CamKII (Cell Signaling), anti-pCamkII (Cell Signaling), anti-β-Actin (Abcam), anti-pErk (Cell Signaling), anti-Biotin (Cell Signaling), anti-Streptavidin-647 (Invitrogen), anti-MAP2 (NeuroMab), anti-Tubulin (Cell Signaling), anti-GluR1 (Cell Signaling).

Mice.

All animal procedures were performed under protocols compliant and approved by the Institutional Animal Care and Use Committees of The Johns Hopkins University School of Medicine. Wild type C57B1/6 mice were obtained from Charles River laboratories (stock number 027).

Mouse cortical and hippocampal neurons were prepared from E16 C57B1/6 mouse embryos as previously described (Cell 143: 442-455 (2010)). Hippocampal neurons were maintained in Neurobasal Medium (Invitrogen) supplemented with 2% B27 (Invitrogen), penicillin/streptomycin (100 U/mL and 100 µg/mL, respectively), and 2 mM glutamine. Dissociated neurons were transfected using the Lipofectamine method (Invitrogen) according to the manufacturer's suggestions.

Cell Culture.

HEK293T and Neuro2A cells were cultured in DMEM supplemented with 10% fetal bovine serum, 2 mM glutamine (Sigma), and penicillin/streptomycin (100 U/mL and 100 µg/mL, respectively; Sigma). Mouse cortical and hippocampal neurons were prepared from E17.5 C57B1/6 mouse embryos as previously described (Cell 143, 442-455 2010). Neurons were maintained in Neurobasal Medium (Invitrogen) supplemented with 2% B-27 (Invitrogen), penicillin/streptomycin (100 U/mL and 100 μg/mL, respectively), and 2 mM glutamine. Dissociated neurons were transfected using the Lipofectamine method (Invitrogen) according to the manufacturer's suggestions.

Pulse-Chase Labeling.

Cortical neurons were cultured for 12-18 days in vitro. Neurons were membrane depolarized with 55 mM extracellular KCl by addition of prewarmed depolarization buffer (55 mM KCl, 0.2 mM $CaCl_2$), 1 mM $MgCl_2$, 10 mM HEPES pH7.5) or a mock buffer (55 mM NaCl, final) in fresh neuronal growth media as previously described (Nature 455: 1198-1204 (2008)). Labeling was done in Neurobasal growth media with B27 supplement and without methionine or cysteine (Life Technologies, special order). $^{35}S$ methionine-cysteine (EasyTag PerkinElmer) was incorporated at 55 mCi in the cys/met free growth medium. Where indicated, MG132 (25 mM, Cell Signaling) and ATPγS (1 mM, Sigma) was added during the radioactive labeling window, 15 minutes prior to stimulation and was kept in for the duration of the stimulation.

For any chase experiment, free radioactivity was washed out with phosphate-buffered saline and replaced with fresh neuronal growth medium. Time points were taken by removing medium and immediately lysing in RIPA buffer (50 mM Tris pH 8.0, 150 mM NaCl, 1% Triton X-100, 0.5% Sodium Deoxycholate, 0.1% SDS, 5 mM EDTA, 10 mM NaF, complete protease inhibitor cocktail tablet (Roche), 1 mM sodium orthovanadate, 1 mM β-glycerophosphate). SDS sample buffer was added and samples were boiled for 5 minutes prior to loading onto SDS-PAGE gels.

Surface Biotin-Labeling, Cell Lysis, Streptavidin Pulldown, Proteasome Purification, and Western Blots.

Surface biotin-labeling was performed as previously described (Nat Neurosci 12, 879-887 2009). Whole mouse brains, cultured cells or whole animal tissue were obtained where indicated and each sample was labeled using Sulfo-NHS-LC-Biotin (ThermoFisher). Cultured cells were washed in pH 8.0 PBS (Gibco) with 1 mM $CaCl_2$) and 2 mM $MgCl_2$ (PBSCM) and treated with 1 mg/mL Sulfo-NHS-LC-Biotin dissolved in PBSCM for 20 minutes at 4° C. before the reaction was quenched for 10 minutes in 50 mM glycine in PBSCM. Intact tissue was quickly and manually chopped, following biotinylation for only 10 minutes at 4° C. in 0.5 mg/mL Sulfo-NHS-LC-Biotin prior to quenching the reaction.

Whole mouse tissues and cultured neurons were collected and homogenized in RIPA buffer (50 mM Tris pH 8.0, 150 mM NaCl, 1% Triton X-100, 0.5% Sodium Deoxycholate, 0.1% SDS, 5 mM EDTA, complete protease inhibitor cocktail tablet (Roche), 1 mM β-glycerophosphate).

Primary, human central nervous system (CNS) tissue, gestational weeks 19-21, were obtained under surgical written consent following protocols approved by the Johns Hopkins Institutional Review Board, based on its designation as biological waste. Tissue was mechanically chopped at 4° C., and immediately processed for surface biotinylation. For streptavidin pulldown experiments lysed cells were incubated with high capacity streptavidin agarose beads overnight and then washed thrice with RIPA buffer before resuspension in SDS sample buffer.

For proteasome purification, cells were treated and then immediately put on ice before purifications were performed as previously described (Biochemistry 48: 2538-2549 (2009)). Briefly, supernatants were incubated with GST-Ub1 (1-3 mg) or 20S purification antibody Kit (Enzo) for 2 hours at 4° C., followed for 1 hour, and washed three times with ice-cold RIPA buffer.

For western blots, samples were boiled for 5 minutes in SDS sample buffer, resolved by SDS PAGE, transferred to nitrocellulose, and immunoblotted. For time course studies, cortical neurons were biotin labeled and homogenized for western analysis as described above. For experiments in HEK293T and Neuro2A cells, samples were boiled for 10 minutes in 1% SDS buffer and diluted 1:5 in 1.25× RIPA buffer prior to loading on gel.

In some embodiments, proteasome purification was performed as follows. Cells were treated and then immediately put on ice before purifications were performed as previously described (Methods Mol Biol 832, 423-432, 2012). Briefly, proteasomes were purified out of neuronal cytosol and detergent-extracted neuronal plasma membranes using the 20S proteasome purification kit (Enzo Life Sciences) or the 26S proteasome purification kit (UBPBio). For western blots, samples were denatured at 65° C. for 5 minutes in SDS sample buffer, resolved by SDS PAGE, transferred to nitrocellulose, and immunoblotted. For catalytic activity assays, ⅙th of the bead volume following proteasome purification was resuspended in activity assay buffer (20 mM Tris-HCl, pH8.0, 5 mM ATP, 5 mM $MgCl_2$, 1 mM DTT). 26S proteasomal activity was assessed by the addition of 10 μM of SUC-LLVY-AMC (Enzo Life Sciences). The contribution of 20S proteasomal activity was assessed by the comparison of 26S proteasome activity to that of total proteasome activity (26S+20S), measured by the activity of samples containing SDS at a final concentration of 0.05%.

Immunocytochemistry.

Neurons were fixed for 5 minutes at 25° C. with 4% paraformaldehyde/4% sucrose in PBS For SNAPP imaging, fixed neurons were incubated with Chicken anti-MAP2 antibodies (1:2000 each) and Goat anti-β2,5 proteasome subunit antibodies (1:500) in 1×permeabilizing GDB (30 mM phosphate buffer pH 7.4 containing 0.2% gelatin, 0.2% Saponin, and 0.8 M NaCl) or 1×non-permeabilizing GDB (30 mM phosphate buffer pH 7.4 containing 0.2% gelatin, and 0.8 M NaCl) overnight at 4° C. Donkey anti-goat AF-555 and donkey anti-chicken AF-488 (1:500 each in 1×GDB for 1 hour at 25° C.) antibodies were used to visualize the primary antibodies. Samples on coverslips were mounted on glass slides using Fluoromount-G (Southern Biotech). Neurons were imaged using a laser scanning Zeiss LSM710 microscope. Images are representative maximal Z projections of multiple optical sections.

For protein proteasome imaging experiments fixed neurons were similarly treated using α-β2,5 subunit antibodies raised in goat (1:200). Samples on coverslips were mounted on glass slides using Fluoromount-G (Southern Biotech). Neurons were imaged using a laser scanning Zeiss Pascal microscope.

Immuno-Electron Microscopy and Analysis.

Cells were fixed in 1.5% glutaraldehyde (EM grade, Pella) buffered with 70 mM sodium cacodylate containing 3 mM $MgCl_2$ (356 mOsmols pH 7.2), for 1 hour at room temperature. Following a 30 minute buffer rinse (100 mM cacodylate 3% sucrose 3 mM $MgCl_2$, 316 mOsmols, pH 7.2), samples were post-fixed in 1.5% potassium ferrocyanide reduced 1% osmium tetroxide in 100 mM cacodylate containing 3 mM $MgCl_2$, for 1 hr in the dark at 4C. After en-bloc staining with filtered 0.5% uranyl acetate (aq.), neurons were dehydrated through graded series of ethanols and embedded/cured with Eponate 12 (Pella). A metal hole punch was used to remove 5 mm discs from the polymerized plates. Discs were mounted onto epon blanks and trimmed. Sections were cut on a Reichert Ultra cut E with a Diatome diamond knife. 80 nm sections were picked up on formvar coated 200 mesh nickel grids and treated for antigen removal followed by on grid immunolabelling. Grids were floated on 95° C. citrate buffer pH 6.0 in a porcelain staining dish for 25 minutes, and then allowed to cool on the same solution for 20 min. After a brief series of 50 mM TBS rinses, grids were floated on 50 mM $NH_4Cl$ in TBS, blocked with 2% horse serum in TBS (no tween) for 20 minutes. Grids were incubated in primary antibody diluted in blocking solution (1-50 Goat antibody). Grids incubated in 1-50 Anti-biotin were diluted in 2% normal goat serum, overnight at 4° C. Grids incubated on blocking solutions served as negative controls. Sections were allowed to come to room temperature (1 hour) on antibody solutions and placed on appropriated blocking solutions for 10 min. After further TBS rinses, grids were floated upon 12 nm Au conjugated donkey anti-goat or 12 nm Au conjugated goat anti-rabbit (Jackson Immunoresearch) at 1-40 dilutions in TBS for 2 hours at room temperature. Grids were then rinsed in TBS, floated upon 1% glutaraldehyde for 5 min, rinsed again and stained with 2% filtered uranyl acetate. All grids were viewed with a Phillips CM 120 TEM operating at 80 Kv and images were captured with an XR 80-8 Megapixel CCD camera by AMT.

Cellular Fractionation.

For fractionation experiments, linear sucrose gradients ranging from 4-20% sucrose were made by layering equal volumes of 15% and 45% sucrose with protease inhibitor in an ultracentrifuge tube and then using a GradientMaster (Biocomp) to linearize the sucrose gradient. Four plates of neurons stimulated, Cycloheximide (5 mM) was briefly added to stop translation, and neurons were rapidly lysed in a sucrose buffer (0.32 M sucrose, 5 mM HEPES, 0.1 mM EDTA, 25 mM DTT) following stimulation, and layered over the sucrose gradient. Samples were subjected to high-speed ultracentrifugation at 40000 RPM for 2 hours. 500 ul fractions were taken and analyzed by SDS-PAGE and western blotting.

For cellular fractionation experiments to determine the membrane attachment of the proteasome, cultured neurons were lysed in either a sucrose buffer (0.32 M sucrose, 5 mM HEPES, 0.1 mM EDTA, 0.25 mM DTT) or hypotonic lysis buffer (5 mM HEPES, 2 mM ATP, 1 mM $MgCl_2$) collected. Nuclei were pelleted at 800 RPM for 5 minutes, and the supernatant containing plasma membranes was pelleted at 55,000 RPM for 1 hour. Once the supernatant (cytosolic fraction) was set aside, the pellet was washed 2× with lysis buffer, and then resuspended in lysis buffer with indicated concentrations of detergent. Following a 15-minute incubation in the buffer, samples were spun down at 55,000 RPM for 1 hour. This was repeated for all indicated concentrations of detergent. Membrane association was determined by classic methods of sodium carbonate extraction. Briefly, purified neuronal plasma membranes were resuspended in 50 mM sodium carbonate, pH 11 and incubated for 30 minutes at 4° C. to strip away membrane associated proteins. Membranes, along with integral membrane proteins, were pelleted at 55000 RPM for 1 hour. Samples were subsequently prepared for SDS-PAGE analysis.

Mass Spectrometry.

Mass spectrometry for interacting partners of the proteasome and of surface proteins was done at the W. M. Keck Foundation Biotechnology Resource Laboratory at Yale University.

SNAPP Collection and Identification.

Following incorporation of radioactive $^{35}S$ methionine/cysteine, and 35 minutes of stimulation in 10 $cm^2$ dishes, neurons were rapidly washed in PBS and fresh Neurobasal media without phenol red and with 2× B-27 supplement was added. At the two-minute time point, all of the media was collected and then spun through a 10 kDa Amicon filter (Millipore) and the flow through was then spun through a 3 kDa Amicon filter (Millipore). The flow through from this sequential filtering was then dialyzed with dialysis tubing with a 100-500 Da cutoff (Spectrum Labs) into either 1× PBS (Gibco) or 20 mM $NH_4HCO_3$ (Sigma). Samples were dialyzed into PBS for the purposes of biotin-tagging and were dialyzed into $NH_4HCO_3$ for both stimulation and for purification. Following dialysis, samples were lyophilized and resuspended in MilliQ water for downstream application.

Quantification of SNAPPs was done by quantifying the amount of radioactivity in each sample by liquid scintillation (Wallac 1410). To determine the nature of SNAPPs, we first separated the SNAPPs by UHPLC on three different chromatography columns optimized for diverse compound chemistries in order to have the broadest detection capabilities of these unknown peptides. Using ultraviolet-visible (UV-vis) spectrophotometry, we were able to detect an abundance of peptides eluting at various times off the different columns, suggesting that SNAPPs contain peptides of varying sizes and hydrophobicity.

SNAPP Labeling and Imaging.

SNAPPs were collected, filtered, and dialyzed into PBS and then were incubated with 1 mg/mL NHS-Biotin (ThermoFisher) overnight at 4° C. The biotin reaction was quenched with 30 mM glycine (Sigma) and biotin-tagged SNAPPs were re-dialyzed to ensure that any unreacted biotin was removed. Purified biotinylated SNAPPs were then used as a reagent for subsequent imaging experiments at a 1:1 ratio (SNAPP-tags: GDB).

Biotin-Epoxomicin.

Biotin-epoxomicin is de-novo synthesized and purchased from Leiden University Institute of Chemistry. Biotin-epoxomicin was added to neuronal cultures at 25 mM immediately after labeling. Preincubation was not necessary. Following SNAPP release assays, treated cells were lysed in a sucrose homogenization buffer (0.32M sucrose, 5 mM HEPES, 0.1 mM EDTA, 0.25 mM DTT). Membranes were separated from the cytosol by high-speed centrifugation at 55,000 RPM for 1 hour. Fractions were solubilized in SDS sample buffer prior to loading on SDS-PAGE gels for western analysis. EM processing was done after 5 minutes of treatment with Biotin-Epoxomicin.

Calcium Imaging.

Calcium imaging was performed as previously described (Neuron 81, 873-887, 2014). Briefly, for the Biotin-Epoxomicin experiments, cultured embryonic cortical neurons were transfected with 1 μg of a mammalian expression construct encoding GCaMP3 at DIV10 and imaged at DIV 12-14. Bicuculline treatment was administered as a 1 μM stimulation in calcium imaging buffer in a perfusion setup. Once the bicuculline stimulation was washed out, biotin-epoxomicin (25 μM) was co-administered with 1 μM Bicuculline in calcium imaging buffer. Each treatment was monitored for three minutes prior to washout. Coverslips were not imaged twice due to Biotin-Epoxomicin being a covalent inhibitor. Cells were ensured to be healthy at the end of the imaging process by stimulating with 55 mM KCl and washing out and assessing for a proper calcium signal. Quantification was done by picking multiple regions of interests in primary and secondary dendrites across multiple coverslips over different imaging days. Data was analyzed using the Time Series Analyzer V3.0 ImageJ plugin and the ROI manager. Data were pooled for all the ROIs to generate a single N value. Brains from P0-P3 mouse pups (Cre GCaMP3; Nestin-Cre ER) were dissected and plated in Neurobasal-A with B-27 supplement for two weeks. At DIV7, 4-hydroxytamoxifen (4-HT, concentration) was added to induce GCaMP expression. Neurons were imaged in a calcium-imaging buffer (130 mM NaCl, 3 mM KCl, 2.5 mM $CaCl_2$), 0.6 mM $MgCl_2$, 10 mM Hepes, 10 mM glucose, 1.2 mM $NaHCO_3$ pH 7.45). Peptides were collected, filtered, and dialyzed and then lyophilized prior to resuspension in 1 mL of MilliQ water and addition onto GCaMP-encoding neurons. 5 µl of resuspended peptides were sufficient to induce the described calcium-induced effects. Peptides treated with Proteinase K were spun through a 10 kDa MW cutoff filter prior to addition onto neurons in order to remove Proteinase K. Random peptide mixtures contained HIV-TAT, a polybasic peptide mixture, or a crude peptide prep.

Human Brain Samples.

All human tissue handling was performed under protocols compliant and approved by the The Johns Hopkins University School of Medicine.

Example 1

A catalytically active 20S proteasome is integral to neuronal plasma membranes.

Figure 1B:
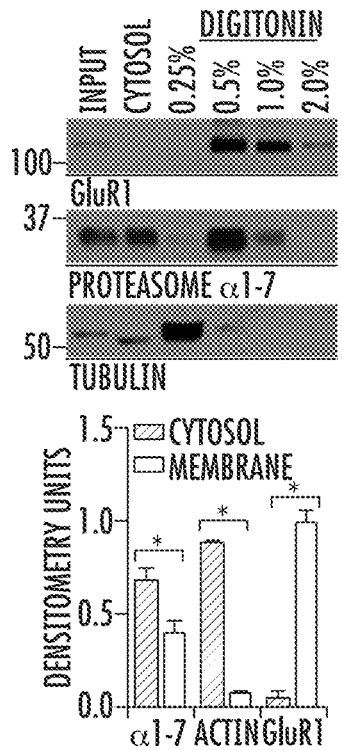
Figure 1C:
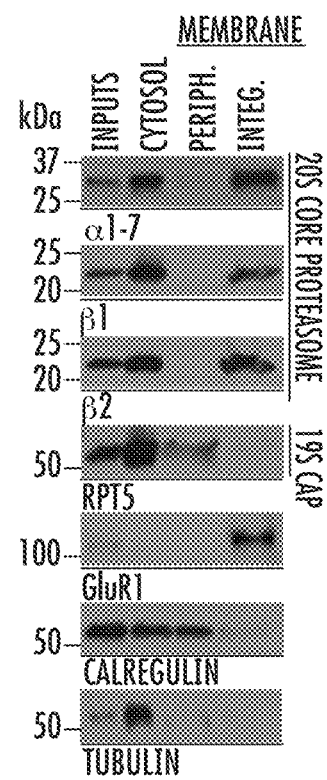

Previous studies attempting to ascribe proteasomes with distinct function in the nervous system have identified localization as a key feature of determining proteasome function. However, all of these studies have focused on the 26S proteasome, either through the use of fluorescently-tagged cap subunits, or have used complex electron microscopy approaches to assess the distribution of 26S capped proteasomes in neurons. Taking a more unbiased approach to evaluate localization of all proteasomes in the nervous system, the inventors performed an immunogold electron microscopy (Immuno-EM) analysis of cortical neuronal cultures using an antibody that detects β2, a core proteasomal subunit common to all catalytically active proteasomes. Since core proteasome subunits have never been shown to be separated from the rest of the macromolecular proteasome complex, these data likely reflected the localization of intact proteasome complexes. While we observed diverse subcellular localization of β2-subunits in neuronal cells, as previously reported, we made the unexpected observation that 42±3% of all gold particles localized to the neuronal plasma membrane (FIG. 1A). We did not see similar localization in heterologous non-neuronal cells. Closer analyses of our Immuno-EM data revealed plasma membrane-localized β2-subunits as integral to plasma membranes (43±3%) and/or peripheral to membranes at the intracellular face (39±2%) (FIG. 1A). This localization suggested that proteasomes were interacting with the plasma membrane, a surprising and never-before seen phenomenon. These data were corroborated by an orthogonal biochemical method that demonstrated that upon separating neuronal plasma membranes from the cytosol, a large fraction (40±2%) of another set of core proteasome subunits, $α_{1-7}$, were localized to plasma membranes (FIG. 1B). To further characterize the biochemical nature of proteasome-plasma membrane interaction, we fractionated neuronal cultures into cytosolic, peripherally membrane-associated, and integral-membrane proteins. Immunoblotting these fractions showed that core 20S proteasome components were, in fact, integral and not peripheral to plasma membranes, whereas 26S cap components were primarily cytosolic (FIG. 1C).

Figure 1D:
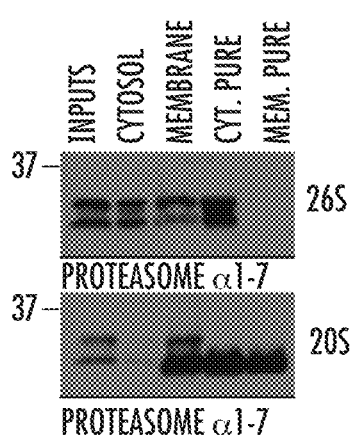

To assess whether the proteasome subunits we observed in the neuronal plasma membrane constituted intact 20S proteasomes, we attempted to purify proteasomes out of the plasma membrane using two different affinity methods. While both 20S and capped-26S affinity purification matrices were able to isolate proteasomes out of the cytosol, only the 20S purification matrix was able to purify proteasomes out of membranes (FIG. 1D). These data indicated that a membrane complex made up of core 20S proteasomal subunits is molecularly distinct from cytosolic proteasomes and can be purified together as a proteasome holocomplex that may be functional. As such, we henceforth referred to this neuronal membrane proteasome as the NMP.

Figure 1E:
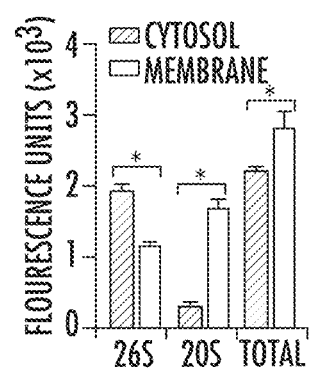

To test whether the NMP was catalytically active, we purified NMPs from neuronal plasma membranes using a 20S purification matrix and incubated them with nonlimiting concentration of a specific substrate that fluoresces upon proteasomal chymotrypsin-like cleavage. We determined, in vitro, that the NMP retained a similar degree of catalytic activity to that of cytosolic proteasomes (FIG. 1E). Interestingly, the catalytic activity of the NMP was potently stimulated by the presence of a low concentration of sodium-dodecyl-sulfate (SDS) (FIG. 1E), a characteristic property of uncapped 20S proteasomes as SDS has been shown to open the gating mechanism of the 20S proteasome without denaturing the holocomplex.

These findings were highly intriguing; while proteasomes have been proposed to interact with the ER membrane, no study has reported proteasome subunits to localize at or be integral to plasma membranes. Considering that the plasma membrane is the site at which the neuron interfaces with the extracellular environment and serves as a critical signaling hub, we hypothesized that the NMP may mediate rapid proteasome-dependent effects on neuronal signaling. However, from the data thus far, it was unclear how the NMP could transduce signals from the neuron to the extracellular space, or vice versa. To interrogate this possibility, we focused on another curious aspect of our Immuno-EM data, which indicated that a significant fraction (18±2%) of proteasomes appeared surface-exposed (FIG. 1A).

Example 2

The NMP is exposed to the extracellular space, is specific to the nervous system, and is temporally regulated.

We postulated that a catalytically active proteasome with access to both the intracellular and extracellular space would be positioned in such a manner to rapidly modulate neuronal function through its proteolytic activity. Thus, to validate our Immuno-EM data, we proceeded with a series of classic approaches to assay whether proteins are exposed to the extracellular space (FIG. 2A). First, cortical neurons were fixed and stained using antibodies against catalytic proteasome subunits under both permeabilizing and non-permeabilizing conditions. Consistent with the NMP being surface exposed, we observed immunostaining against proteasomal subunits under both conditions, but only observed cytosolic MAP2 staining under permeabilizing conditions (FIG. 2A). To biochemically determine whether the NMP was surface-exposed, we found that proteasome subunits in neuronal membranes were susceptible to proteolysis by extracellular application of the broad spectrum serine protease, Proteinase K (PK), to cultured cortical neurons, whereas cytosolic proteasome subunits were protected from protease cleavage (FIG. 2B). As an orthogonal method of identifying surface exposed proteins, we turned to previously described surface-biotinylation/purification approaches. Briefly, cortical neuronal cultures were treated with a cell-impermeable reactive biotin-NHS-ester to exclusively and covalently label proteins that contained epitopes that were exposed to the extracellular space. We confirmed that a host of core 20S proteasome subunits could be isolated from these surface-biotinylated neuronal lysates on streptavidin beads, providing further evidence that the NMP was exposed to the extracellular space (FIG. 2C). We did not detect a key 26S cap protein Rpt5 or contamination from abundant cytosolic proteins in our surface-biotinylated pulldowns (FIG. 2C). Similar results were observed in human neurons, demonstrating the conservation of these findings across mammals (Figure S2A). Extending these findings in vivo, we determined that the expression of the surface-exposed NMP was unique to neuronal tissues as compared to five other major organs and heterologous cell lines (FIG. 2D, 2E).

Consistent with NMP expression being unique to the nervous system, we determined that NMP expression paralleled in vivo expression patterns of GluR1, a neuronal-specific ionotropic receptor whose expression functionally correlates with critical stages in neuronal development. Performing the same experiments in vitro, we observed that the NMP was expressed in neurons at 8 days in vitro (DIV), but not prior, indicating a clear temporal shift in proteasome expression at the plasma membrane (FIG. 2F). These experiments demonstrated that our experimental approach to isolate surface-exposed proteasome components is not contaminated by cytosolic proteasome expression, as total proteasome expression is abundant in neurons younger than 8 DIV even though surface expression is absent. Taking advantage of this temporal regulation of NMP expression, we used comparative liquid-chromatography/mass-spectrometry of surface-biotinylated samples from neurons at 8 DIV, compared to 7 DIV, to determine the complete composition of the NMP. This analysis revealed the expected result that the NMP contained almost all core 20S subunits (FIG. 2G), thus indicating that the NMP was a complete 20S proteasome integral to plasma membranes and exposed to the extracellular space.

Our data suggested that the NMP was oriented in such a manner that it would have access to both the intracellular and extracellular space to possibly perform some form of transmembrane signaling. It remained to be determined whether this form of signaling existed, how it was manifested, and what its function was.

Example 3

Figure 3C:
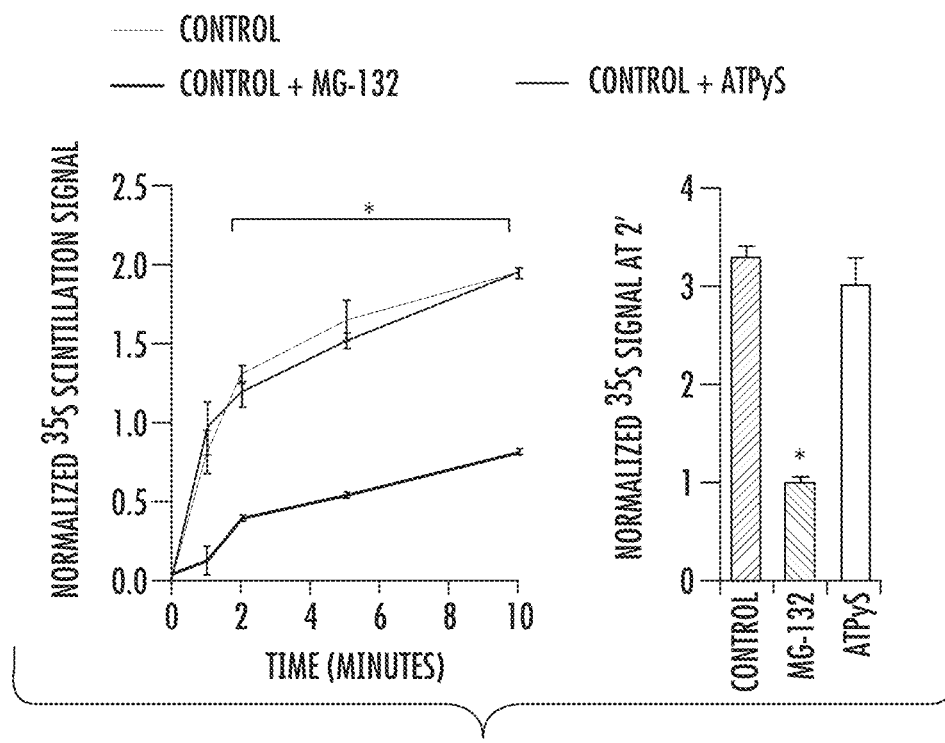
Figure 3D:
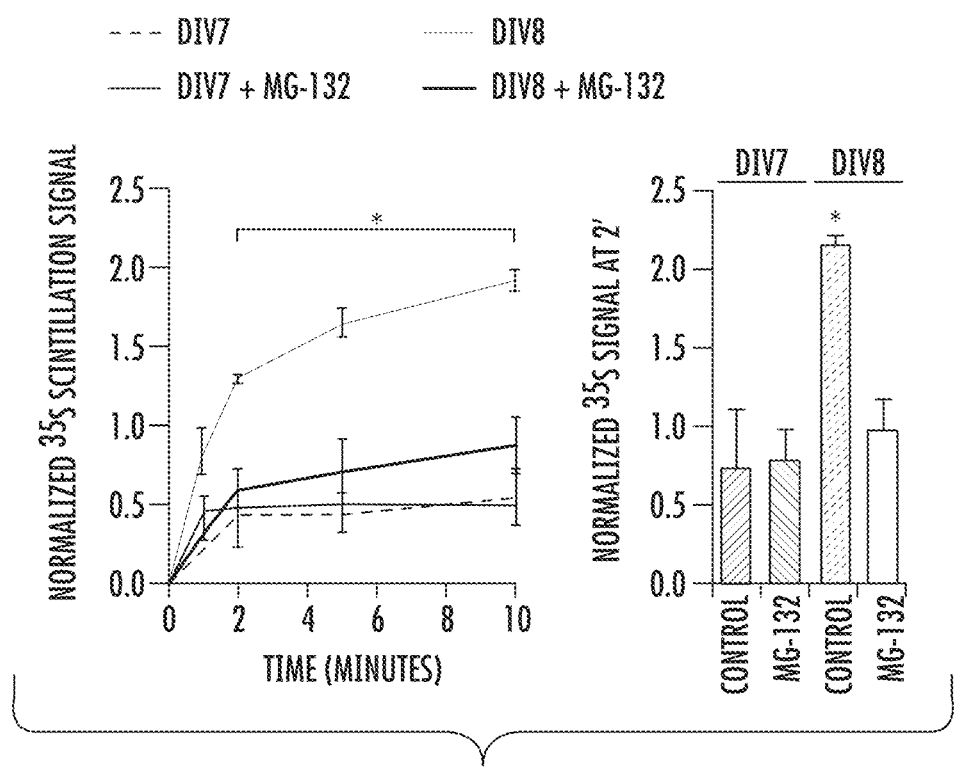

The NMP mediates degradation of intracellular proteins into extracellular peptides Given that it was catalytically active in vitro, we hypothesized that in intact cells, the NMP would promote proteasome-dependent degradation of intracellular proteins into the extracellular space. To test our hypothesis, we used 35S-radiolabelling approaches to trace the fate of newly synthesized intracellular proteins (Schubert et al., 2000). 35S-methionine/cysteine was quickly incorporated into neurons; addition of proteasome inhibitors had no effect on radiolabeling efficiency (FIG. 3A). After 10 minutes of radiolabeling, free radioactivity was washed away, and media was collected over a time course and analyzed by liquid scintillation. We observed rapid proteasome-dependent release of radioactivity into the culture medium. Of the released radioactive material, 90±3% was made up of Proteinase K-sensitive molecules that ranged between 500 and 3000 Daltons in size (FIG. 3B). From this, we concluded that the radioactivity in the media was composed of protein peptides derived from the proteasome (Kisselev et al., 1998) and not individual amino acids or small molecules. This is consistent with the model that the NMP was degrading intracellular proteins into extracellular peptides, since proteasome cleavage products are peptides between 500 and 3000 Da in size. In further support of the NMP acting as a 20S proteasome complex, release of radioactive material into the extracellular space was not dependent on ATP hydrolysis, another key characteristic of functional 20S proteasomes (FIG. 3C). While these data agreed with our hypothesis that the NMP is responsible for this transmembrane degradation, our data thus far did not discriminate between cytosolic and membrane proteasomes. Taking advantage of the temporal expression of the NMP between 7 DIV and 8 DIV, we observed that proteasome-dependent release of radioactivity into the media paralleled the temporal expression of the NMP (FIG. 3D). Again, this experimental paradigm demonstrates that the release of radioactivity was both regulated and dependent upon proteasome function. Moreover, we observed release of radioactivity in 8 DIV neurons compared to 7 DIV neurons, despite the presence of cytosolic proteasomes at both 7 DIV and 8 DIV. Therefore, these data suggested that the NMP may be responsible for the direct conversion of intracellular proteins into extracellular peptides.

Example 4

Figure 4A:
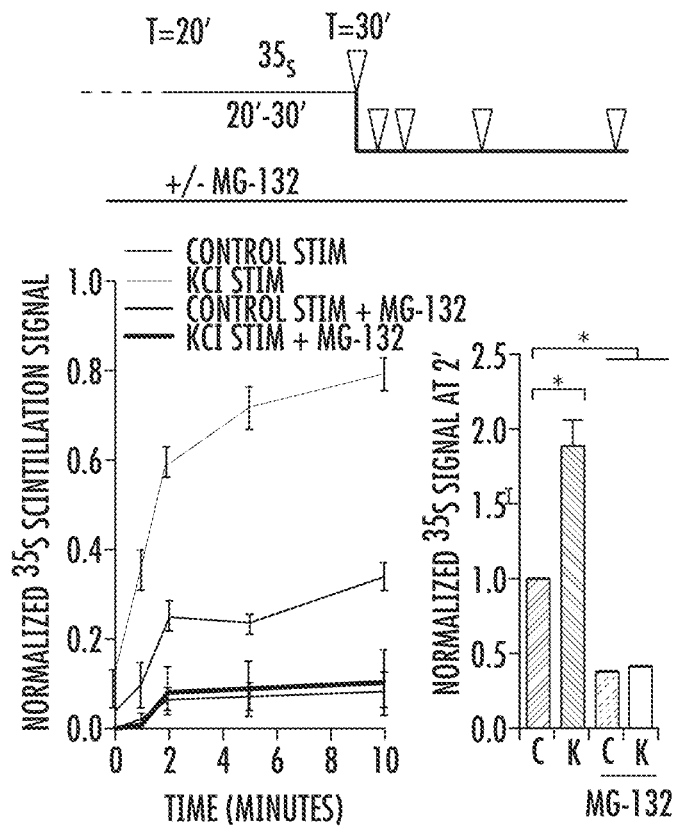
FIGS. 4A-4F show neuronal activity induces Proteasome-mediated degradation of synthesized proteins to generate signaling peptides that are secreted from the neuron. (A) Pulse chase schematic and collection paradigm for release of radioactive material into media. Following the indicated stimulation and radioactive pulse, cells were rapidly washed with PBS, and chased into nonradioactive media, either in the presence of absence of MG-132. White arrowheads indicate times when a 25 µl sample was withdrawn from the media for scintillation analysis. Cumulative data are shown for the 10 minute time course on the left and at the 2 minute time point on the right (n=5, p<0.01). (B) Schematic for collection, purification, and use of SNAPPs. Following 30 minutes of stimulation, media containing the stimulation buffer is washed out and replaced with non-depolarizing collection media. Following quantification of radioactivity in the media as described above, SNAPPs are purified out of the media (see Examples), and either applied directly onto cells or labeled in vitro for tagging. (C) SNAPPs induce calcium transients. Representative images on the left demonstrate an increase in fluorescence of a calcium reporter upon addition of SNAPPs to naive GCaMP3-encoding neurons. Quantification is on the right, where the first arrowhead indicates when SNAPPs are added and the second arrowhead indicates time of washout (n=8, p<0.01). Control SNAPPs are purified from neurons with baseline spontaneous levels of activity. (D) SNAPPs potentiate calcium-sensitive signaling. Western blot of phosphorylated CamKII, total CamKII, and Actin following addition of SNAPPs or KCl stimulation for five minutes. Western blot of pERK1/2 following incubation with control peptides or SNAPPs and with or without pretreatment of peptides with Proteinase K. (E) Labeled SNAPPs preferentially bind stimulated neurons. Unstimulated (control) or stimulated (KCl) neurons were fixed and stained with MAP2 (Green) and labeled SNAPPs (Magenta). (F) Channelrhodopsin (ChR2) transfected neurons were stimulated at the indicated frequency for one minute, fixed, and stained with an anti-GFP antibody that is reactive against ChR2 protein (Green) and labeled SNAPPs (Magenta).

Given the importance of proteasomes during neuronal stimulation, we considered that during neuronal activity proteins may be more rapidly processed by the proteasome and the processed peptides were secreted from the neurons into the media. To test this idea, we quantified the radioactivity in the media following stimulation, and consistent with our hypothesis, we observe a stimulation-induced increase in the radioactivity in the media (FIG. 4A). In contrast, inhibition of activity dependent pathways blocked this release in neurons undergoing spontaneous activity. Based on the size and nature of these peptides, we believe them to not contain any previously discovered neurotrophic factors, which are larger than 3 kDa. In addition, the rapid time kinetics of peptide release and the fact that a majority of these peptides derive from the proteasome suggest that they are not in known classes of neuropeptides. Canonical neuropeptides require extensive modifications and cleavage events that are inconsistent with our time kinetics; moreover, these cleavage events are not mediated by the proteasome and are not able to be inhibited by proteasome inhibitors such as MG-132. Intriguingly, the production and release of these non-canonical peptides seems to be restricted to the nervous system, as other cell types we have tested do not exhibit this phenomenon (data not shown). Given that these peptides represent novel peptides specific to the nervous system related to aspects of neuronal activity we will refer to these peptides as secreted neuronal-activity induced proteasomal peptides or SNAPPs.

To determine the nature of these SNAPPs, we first separated the SNAPPs by UHPLC on three different chromatography columns optimized for diverse compound chemistries in order to have the broadest detection capabilities of these unknown peptides. Using ultraviolet-visible (UV-vis) spectrophotometry, we were able to detect an abundance of peptides eluting at various times off the different columns, suggesting that SNAPPs contain peptides of varying sizes and hydrophobicity. Interestingly, biological replicates show similar SNAPP profiles indicating that the specific sequences generated may be regulated.

Figure 4B:
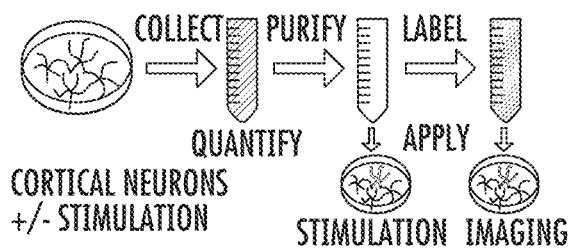
Figure 4C:
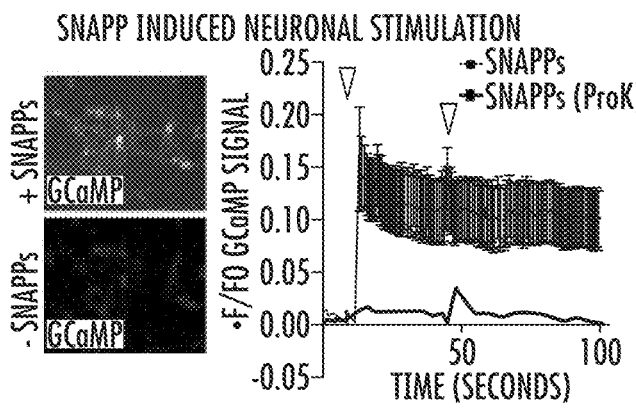
Figure 4D:
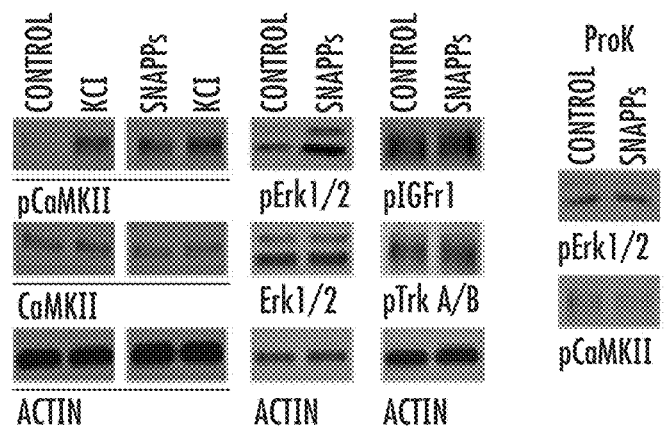
Figure 4E:
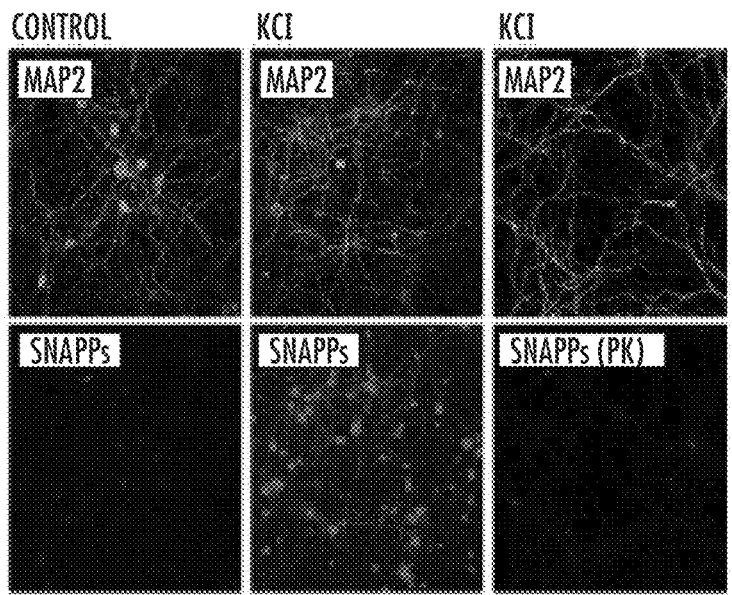
Figure 4F:
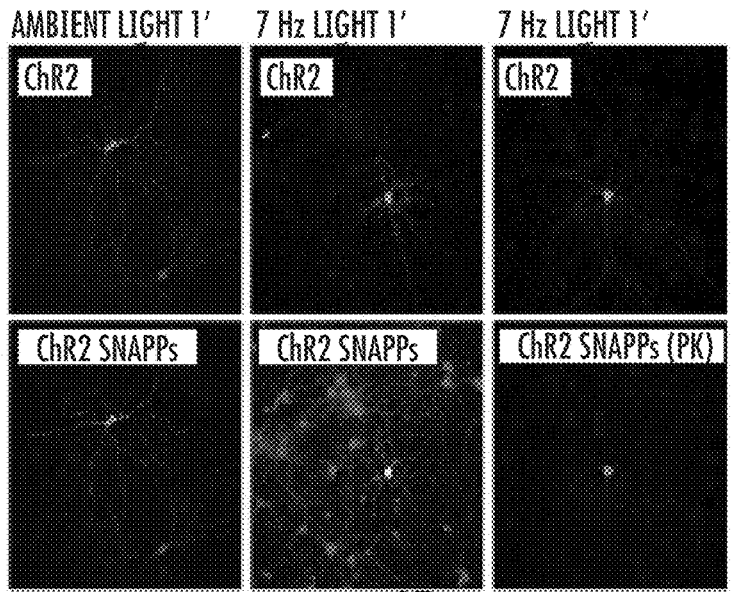

Considering SNAPPs were endogenous molecules being released from neurons following stimulation, we sought to determine their biological significance en masse. To test the biological significance of SNAPPs we purified and added them onto naive cells to determine if they had any capacity to induce neuronal signaling (FIG. 4B). Mice encoding a ubiquitously expressed genetically encoded calcium indicator, GCaMP3, were sacrificed and cortices were dissected and cultured. GCaMP encoding neurons were perfused with SNAPPs for one minute, and then the peptides were washed out. Calcium imaging over this time-course demonstrates that SNAPPs induced calcium transients that were sustained for several minutes even following removal of the SNAPPs from the perfusion (FIG. 4C). In light of these data, we added these peptides onto DIV14 neurons in culture and looked for stimulation of calcium-sensitive pathways. Consistent with the GCaMP imaging data, we demonstrate that the phospho-CaMKII and phospho-ERK pathways are both stimulated by SNAPPs, but not from material derived from proteinase K treated SNAPPs (FIG. 4D). Moreover, growth factor induced pathways, such as TrkB signaling; do not respond to SNAPP addition, further demonstrating that SNAPPs do not contain known released growth factors (data not shown). To understand further the mechanism by which SNAPPs were acting to stimulate the calcium sensitive pathways, we asked whether they were capable of binding neurons. After isolating and purifying the SNAPPs, we tagged them with biotin, quenched the biotinylation reaction, and made sure to remove all excess biotin with dialysis. We then added these biotin tagged SNAPPs onto fixed cells to identify where they were binding. Intriguingly, we observe that these peptides display an enhanced propensity for binding KCl stimulated neurons over unstimulated neurons (FIG. 4E). This binding capacity is also proteinase K sensitive, further confirming that the binding is due to peptides (data not shown). Media derived from cells stimulated in the presence of proteasome inhibitors does not display this ability to bind neurons, further suggesting that SNAPPs possess the unique capacity for this labeling. Using optogenetic approaches, we sought to determine the sensitivity of this SNAPPs tagging of activated neurons. Channelrhodopsin was sparsely transfected into neuronal culture, and the culture was light stimulated and subsequently stained using SNAPPs. We demonstrate that the stimulated neuron and some neurons surrounding that neuron were marked, but neurons that were not adjacent to the Channelrhodopsin-encoding neuron were not marked using the SNAPPs (FIG. 4F). This was not observed for Channelrhodopsin labeled neurons stimulated with ambient light (FIG. 4F). These data indicate that SNAPPs are a diverse population of activity induced secreted signaling peptides capable of inducing neuronal activity and intriguingly, are able to selectively bind stimulated neurons.

Example 5

Developmentally regulated SNAPP release is tightly correlated with a proteasome expressed at the neuronal membrane.

Figure 5A:
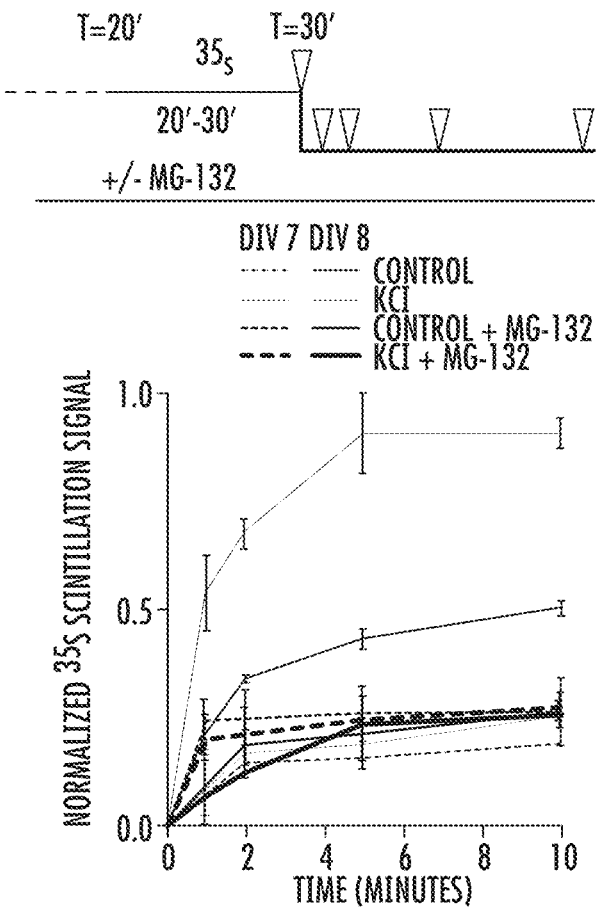
FIGS. 5A-5B show developmentally regulated SNAPP release is tightly correlated with a proteasome expressed at the neuronal membrane. (A) SNAPP release is developmentally regulated. As described in FIG. 3A, SNAPP release was measured at DIV7 and DIV8. (B) Quantification of developmentally regulated SNAPP release is shown at 2 minutes.
Figure 5B:
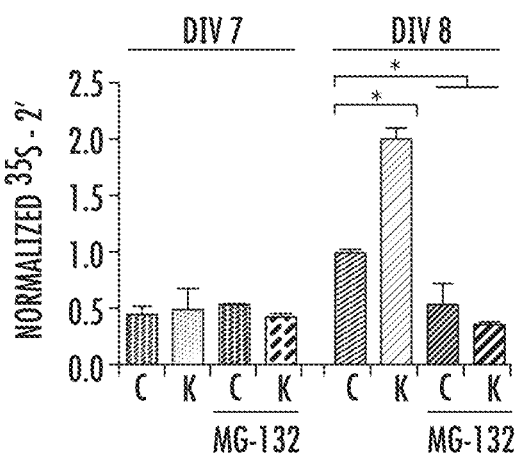
Figure 6A:
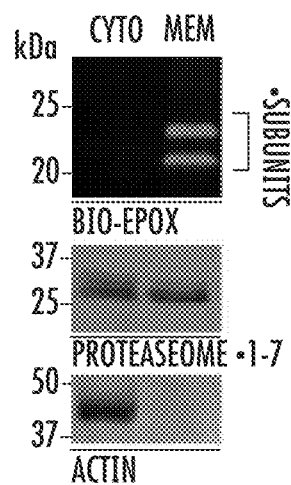
FIGS. 6A-6D show that the NMP is required for release of extracellular peptides and modulates neuronal signaling. (A,B) Biotin-epoxomicin does not cross neuronal membranes and covalently binds proteasome subunits. (A) Neurons treated with biotin-epoxomicin (Bio-Epox) were separated into cytosolic (Cyto) and membrane (Mem) fractions and analyzed by western using fluorescent streptavidin. Immunoblots using indicated antibodies shown below. (B) Immunogold labelling against biotin (yellow arrows) in cultured cortical neurons treated with Bio-Epox, with representative images shown (out of 54). Labeled ultrastructures: presynaptic regions (Pre), postsynaptic regions (Post), Microtubules (MT—black arrowheads), and synaptic vesicles (SV—black arrowheads). Quantification of particles in cytosol and on membrane (right). (C) NMP-specific inhibition blocks release of extracellular peptides. Media collected from neurons following radiolabeling, with or without Bio-Epox. Liquid scintillation quantification of media at indicated time points is shown normalized to control at the 10 minute time point; 2 minute time point shown separately on bar graph. (D) NMP inhibition modulates speed and intensity of neuronal calcium transients. Bicuculline (Bic) added to naïve GCaMP3-encoding neurons, with or without Bio-Epox. Representative images (above) and traces of bicuculline response before and after Bio-Epox addition are plotted. Quantification of normalized fluorescence intensity measurements of calcium signals over imaging time course. Average maximum amplitudes are plotted, and include analysis of calcium signaling after treatment with MG-132. *$P<0.01$ (two-tailed Student's t-test). Data are presented as mean±SEM (b, n=54, >200 gold particles; c, n=3; d, n=2, n=24 neurons, with 18 ROIs analyzed per neuron).
Figure 6B:
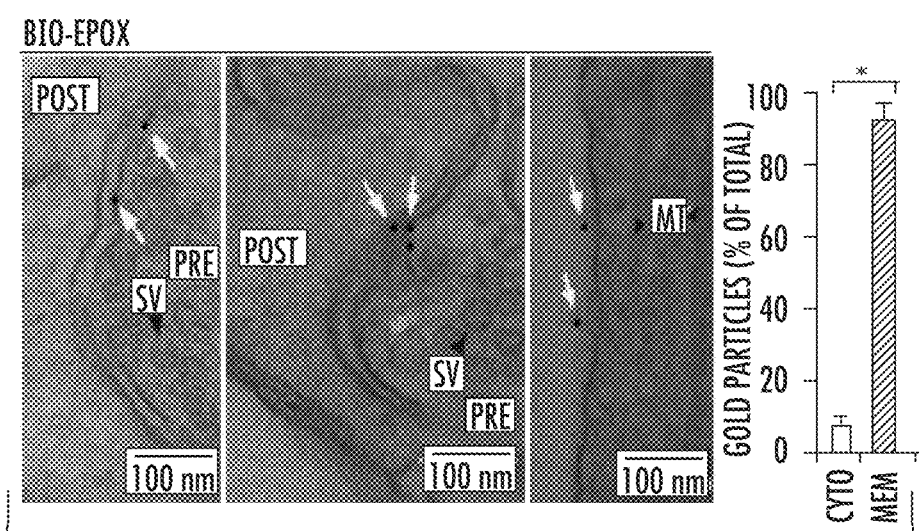
Figure 6C:
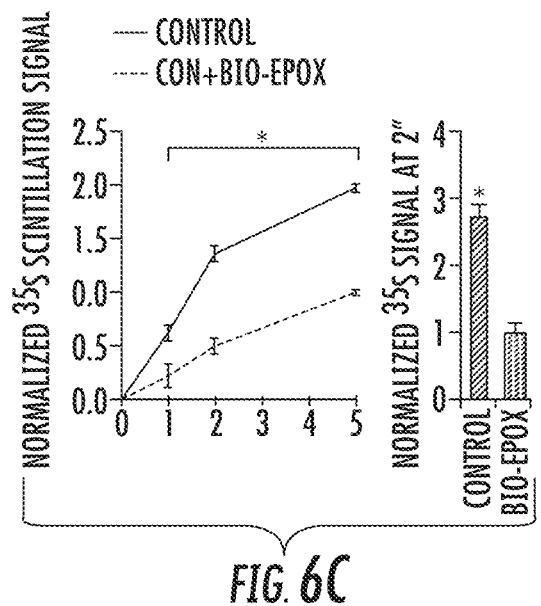
Figure 6D:
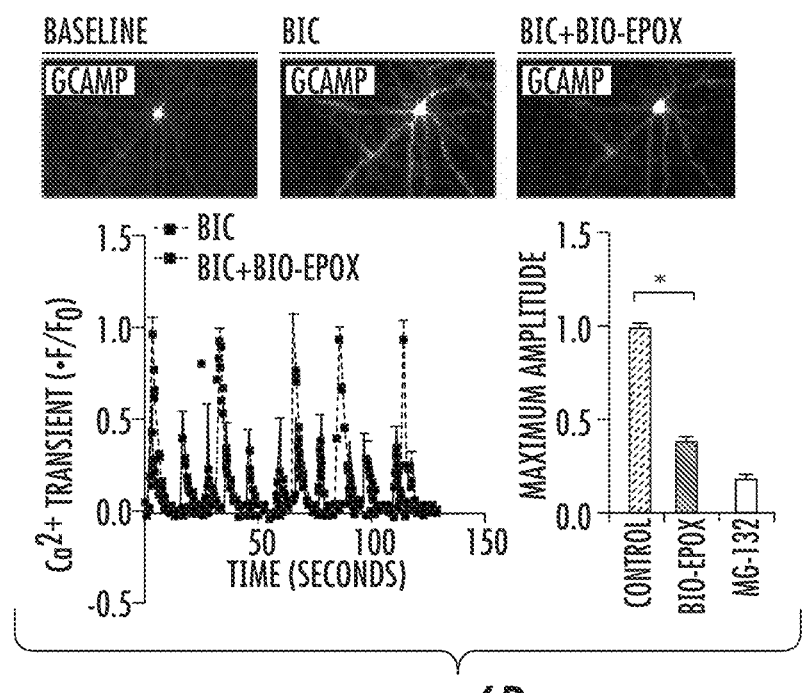

As compared to DIV 8 and older neurons, DIV 7 neurons do not display SNAPP release (FIGS. 5A and 5B). The developmental regulation of both NMP (FIG. 2F) expression and the corresponding release of SNAPPs was the first piece of evidence that indicated to us that the NMP is responsible for SNAPP release.

Example 6

The NMP modulates neuronal activity through the production of extracellular signaling peptides.

To specifically determine the contributions from the NMP in this process of proteasome-directed peptide signaling, separately from the cytosolic proteasome, we identified a chemical tool that was highly selective to the NMP. We found that the addition of a biotin group on the non-reactive portion of epoxomicin, a highly potent, specific, and covalent inhibitor of catalytically active proteasomes generates a new compound (biotin-epoxomicin) that is unable to cross neuronal cell membranes, yet maintains target specificity. Biochemical fractionation of neurons treated with biotin-epoxomicin confirmed that biotin-epoxomicin is indeed membrane-impermeable (FIG. 5A). Furthermore, Immuno-EM analysis of cortical neuronal cultures treated with biotin-epoxomicin showed 91±5% of biotin at plasma membranes (FIG. 5B). Any cytosolic labeling is likely due to the presence of endogenously biotinylated proteins, as we see cytosolic labeling in cultures treated with vehicle control, but an absence of labeling in our secondary-only controls. These data independently confirmed that the membrane proteasome is catalytically active, since epoxomicin requires that the proteasome be active in order to covalently bind to and inhibit the catalytic subunits. Using this inhibitor, we sought to separate the role for the NMP from the role of cytosolic proteasomes in regulating extracellular peptide production. Application of biotin-epoxomicin to radiolabeled cortical neurons led to the acute inhibition of radioactive peptide release into the extracellular space (FIG. 5C). Based on these data, we believe that the endogenous NMP is catalytically active, directly and specifically mediates the degradation of intracellular proteins into extracellular peptides, and that biotin-epoxomicin is a useful tool to study the relevance of the NMP. With this tool validated, we wanted to test our initial hypothesis that membrane-apposed proteasomes may play a role in rapid neuronal signaling.

To test whether the NMP was relevant to aspects of neuronal signaling, changes in intracellular calcium were measured since calcium serves as a rapid readout for many types of neuronal signaling. Calcium imaging was performed using GCaMP3-transfected cultured cortical neurons treated with GABAergic receptor antagonist bicuculline, which relieves inhibition on neuronal circuits, inducing regular firing of action potentials and calcium transients. Addition of biotin-epoxomicin strongly and rapidly attenuated the amplitude of bicuculline-induced calcium transients, similar to that which we observed upon acute addition of MG-132 (FIG. 5D). These data validated our initial hypothesis that membrane-apposition of proteasomes would render them capable of rapidly affecting neuronal signaling. Based on these data, an endogenous function of the NMP is to modulate the strength and speed of activity-dependent neuronal signaling through its proteolytic activity, possibly through the actions of the resulting extracellular peptides. These data are consistent with the NMP producing extracellular peptides capable of modulating neuronal signaling, that we found when titrated onto naïve GCaMP3-encoding neurons are sufficient to induce robust calcium transients within 10 seconds of addition. These data signify that the ability for purified media to stimulate calcium transients in naïve neurons relies upon NMP-mediated release of peptides into the extracellular space.

Example 7

NMP expression is conserved in Humans and varies across individuals.

Fetal human brains were obtained according to Institutional Review Board Protocol. Fresh tissue was dissected and sliced and then surface biotinylated. Surface proteins were isolated on streptavidin beads and subsequently analyzed by western blot. Proteasome subunits were pulled down on streptavidin beads, whereas cytosolic protein actin was not. In FIG. 6, inputs are shown to the left of the streptavidin pulldown. Expression was found to be fairly consistent across humans, except for one sample that demonstrated much higher expression. Further analysis revealed that the patient who consented for the procedure was on regular methadone use for treatment of heroin addiction. These samples were run blinded. Densitometry quantification is shown to the right, with expression of the NMP normalized to the total amount of proteasome.

Example 8

Dysregulation of the NMP in Alzheimer's disease.

NMP expression was measured in mouse cortical neurons treated with a variety of compounds, including $A\beta_{1-42}$. DIV12 mouse neurons were treated with 1 µM $A\beta_{1-42}$ peptide for 12 hours. Following treatment, neurons were surface biotinylated, and surface proteins were isolated and analyzed by western blot (FIG. 7). Inputs are shown to the left of the streptavidin pulldown. There was a significant decrease in expression of proteasome subunits in the streptavidin pulldown from Aβ treated neurons.

Example 9

NMP expression in samples from post-mortem Human patients with Alzheimer's disease.

Figure 9:
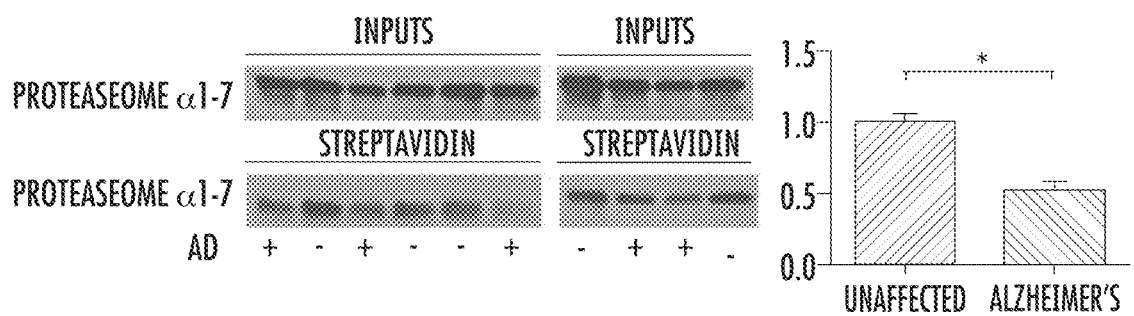
FIG. 9 shows that NMP expression in samples from post-mortem Human patients with Alzheimer's disease. Primary samples from 10 patients were obtained from the Johns Hopkins Lieber Institute for Brain Development Brain Bank. All tissue was obtained under their IRB. Samples were blinded, and then surface biotinylated and lysed. Surface proteins were pulled down on streptavidin beads and analyzed by western blot. Inputs are shown above the streptavidin pulldown. Lower levels of proteasome subunits were seen in 5 different samples, which were revealed to be from patients who had Alzheimer's. Samples are labeled underneath as either AD (+) for AD positive samples or AD (−) for unaffected individuals. This blinded approach confirms the ability to use NMP expression as a diagnostic method for Alzheimer's disease. Quantification is shown to the right, with the levels of the NMP normalized against the total proteasome levels. * $P<0.01$, Student's t-test, n=5.

Primary samples from 10 patients were obtained from the Johns Hopkins Lieber Institute for Brain Development Brain Bank. All tissue was obtained under their IRB. Samples were blinded, and then surface biotinylated and lysed. Surface proteins were pulled down on streptavidin beads and analyzed by western blot. Inputs are shown above the streptavidin pulldown (FIG. 9). Lower expression levels of proteasome subunits were seen in 5 different samples, which were revealed to be from patients who had Alzheimer's. Samples are labeled underneath as either AD (+) for AD positive samples or AD (−) for unaffected individuals. This blinded approach confirms the ability to use NMP expression as a diagnostic method for Alzheimer's disease. Quantification is shown to the right, with the levels of the NMP normalized against the total proteasome levels (FIG. 9). *P<0.01, Student's t-test, n=5.

Example 10

Dysregulation of the NMP in a murine model of Alzheimer's disease.

Figure 10:
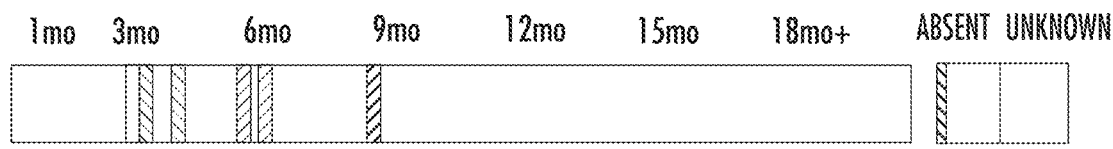
FIG. 10 shows the progression of Alzheimer like symptoms in a mouse model of the disease. Brains from early stage (3 month old) J20 AD mouse model (see figure) and wild type mice were treated as in FIG. 4C to isolate the NMP. Samples were run on SDS-PAGE and probed for proteasome, APP and actin. Note that in AD mouse models at early stages of disease progression we observe an increase in NMP as opposed to a decrease when treating neurons in culture with Abeta or from late stage human AD samples. This indicates that the NMP is dynamic in nature during prior to and during AD progression and can be specifically studied for its contribution to AD related phenotypes in these and other mouse models. The NMP is one of the few proteins ever shown to have such a dramatic change in expression in this AD model so early in development of the disease.
Figure 10:
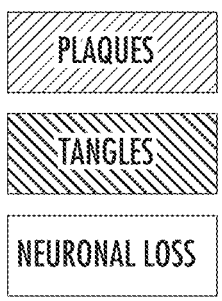
Figure 10:
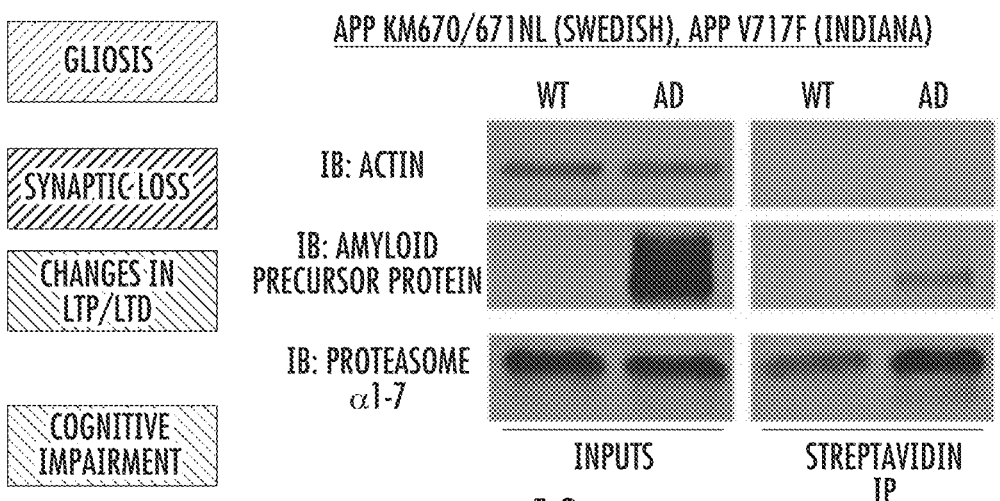

Brains from early stage (3 month old) J20 AD mouse model (see FIG. 10) and wild type mice were treated as in FIG. 4C to isolate the NMP. This stage in development is fairly early in AD progression. Samples were run on SDS-PAGE and probed for proteasome, APP and actin. Note that in AD mouse models at early stages of disease progression we observe an increase in NMP as opposed to a decrease when treating neurons in culture with Aβ or from late stage human AD samples. This indicates that the NMP is dynamic in nature during prior to and during AD progression and can be specifically studied for its contribution to AD related phenotypes in these and other mouse models. The NMP is one of the few proteins ever shown to have such a dramatic change in expression in this AD model so early in development of the disease.

Example 11

Dysregulation of the NMP in a murine model of Huntington's disease.

Figure 11:
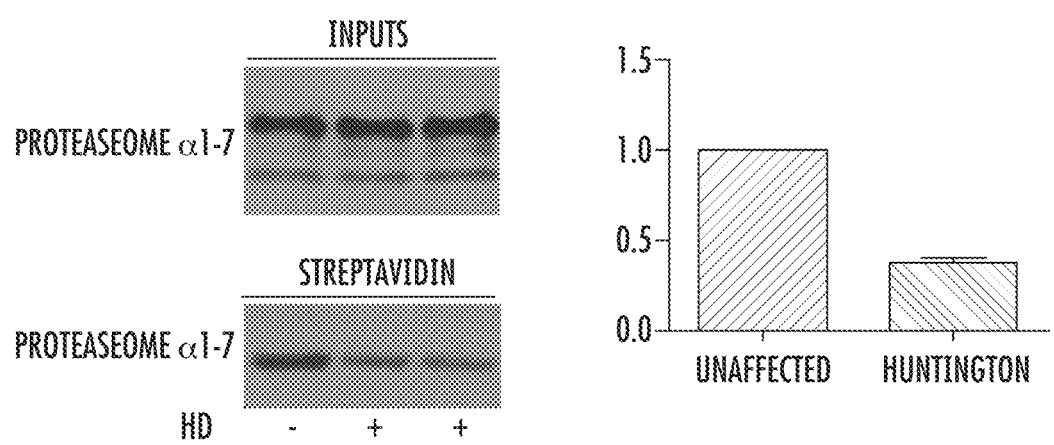
FIG. 11 shows that Dysregulation of the NMP in a murine model of Huntington's disease. The striatum was dissected from 6 week aged Huntington transgenic animals. This stage of development is fairly early in the disease progression of Huntington in these animals, where few robust changes have been detected at this early stage. Dissected tissue was surface biotinylated, and surface proteins were isolated on streptavidin beads. Inputs are shown above streptavidin pulldown. A robust decrease in the levels of the NMP in Huntington positive (+) striatum is shown, and quantified to the right as normalized to input proteasome levels. These data suggest that the NMP may be an early diagnostic in the progression of Huntington's disease.
Figure 12:
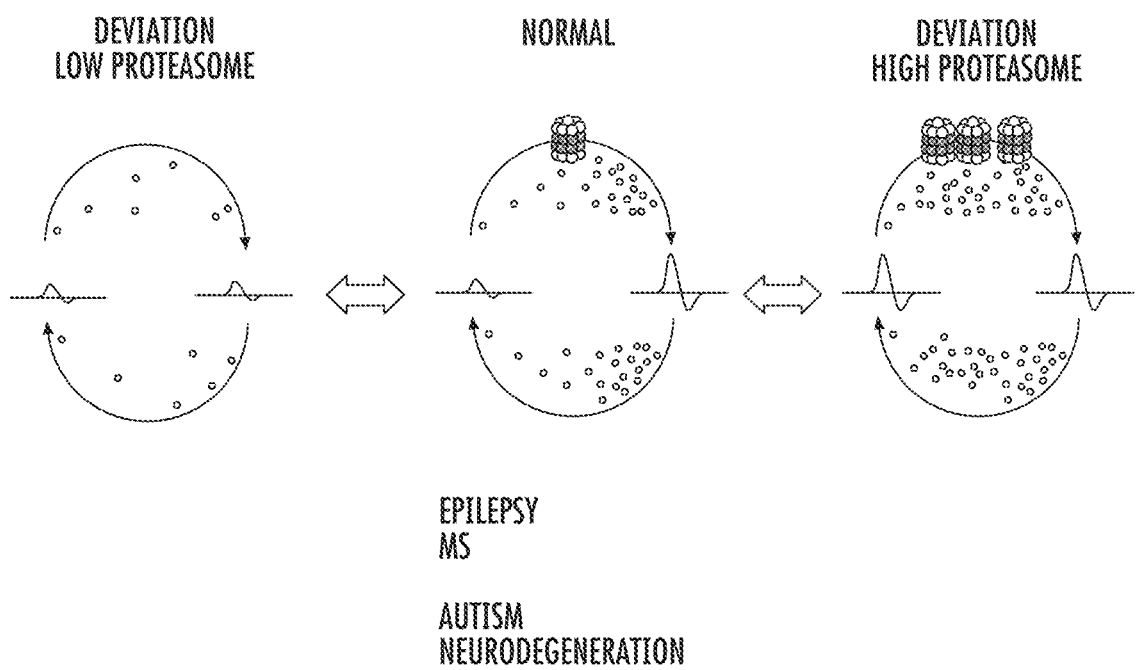
FIG. 12 is a schematic diagram depicting that certain neurological disorders may in fact, be caused by disruption of NMP function or under expression of NMP proteins, causing a decrease in SNAPP production which may cause under stimulation of neural pathways downstream from the affected cells. This could also lead to neuronal dysfunction in the form of neuronal communication deficits via decreased synaptic contacts and/or signaling. Conversely, certain disorders may in fact, be caused by an excess of NMP function or over expression of NMP proteins, causing an increase in SNAPP production which may cause over stimulation of neural pathways downstream from the affected cells, and which may lead to neuronal apoptosis and death.

The striatum was dissected from 6 week aged Huntington transgenic animals. This stage of development is fairly early in the disease progression of Huntington in these animals, where few robust changes have been detected at this early stage. Dissected tissue was surface biotinylated, and surface proteins were isolated on streptavidin beads. Inputs are shown above streptavidin pulldown (FIG. 11). A robust decrease in the levels of the NMP in Huntington positive (+) striatum is shown, and quantified to the right as normalized to input proteasome levels. These data suggest that the NMP may be an early diagnostic in the progression of Huntington's disease.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for screening for compounds which stimulate secretion of neuronal membrane proteasome (NMP) mediated production of secreted neuronal-activity induced proteasomal peptides (SNAPPs) comprising the steps of:
   a) providing a plurality of in vitro cultures comprising a plurality of neurons in a growth medium;
   b) providing one or more test cultures by contacting the neurons of at least a first culture with a test compound for a period of time sufficient to allow NMP mediated production of SNAPPs into the growth medium;
   c) providing a negative control by contacting the neurons of at least a second culture for a period of time sufficient with a carrier or vehicle which will not stimulate NMP mediated production of SNAPPs into the growth medium;
   d) removing at least a portion of the growth medium of the cultures of b) and c) and performing an isolation step to purify the SNAPPs from the cultures of b) and c);
   e) quantifying the amount of SNAPPs isolated in d) from the cultures of b) and c); and
   f) determining that the test compound is a stimulator of NMP and SNAPP production when the quantity of SNAPPs isolated from b) are significantly increased when compared with the amount of SNAPPs in c).

2. The method of claim 1, further comprising the steps of:
   c1) providing a positive control by stimulating the neurons of a first culture for a period of time sufficient with a known neuronal proteasomal stimulant to allow NMP mediated production of SNAPPs into the growth medium;
   d1) removing at least a portion of the growth medium of the cultures of b), c), and c1) and performing an isolation step to purify the SNAPPs from the cultures of b), c), and c1);
   e1) quantifying the amount of SNAPPs isolated in d1) from the cultures of b), c), and c1); and
   f1) determining that the test compound is a stimulator of NMP mediated production of SNAPP secretion when the quantity of SNAPPs isolated from both b) and c1) are significantly increased when compared with the amount of SNAPPs in c).

3. The method of claim 1, wherein the quantification of SNAPPs in the sample is performed using HPLC (LC-MALDI) or fractionation of an HPLC column directly into an electrospray mass spectrometer (LC/MS-ESI).

* * * * *